(12) United States Patent
Tibbe et al.

(10) Patent No.: US 9,638,636 B2
(45) Date of Patent: May 2, 2017

(54) MICROSIEVE DIAGNOSTIC DEVICE IN THE ISOLATION AND ANALYSIS OF SINGLE CELLS

(71) Applicant: VyCAP B.V., Deventer (NL)

(72) Inventors: Arjan Gerhardus Johannes Tibbe, Deventer (NL); Cornelis Johannes Maria van Rijn, Hengelo (NL); Leonardus Wendelinus Mathias Marie Terstappen, Amsterdam (NL)

(73) Assignee: VyCAP B.V., Deventer (NL)

( * ) Notice: Subject to any disclaimer, the term of this patent is extended or adjusted under 35 U.S.C. 154(b) by 225 days.

(21) Appl. No.: 14/404,577

(22) PCT Filed: May 29, 2013

(86) PCT No.: PCT/NL2013/050389
§ 371 (c)(1),
(2) Date: Nov. 28, 2014

(87) PCT Pub. No.: WO2013/180567
PCT Pub. Date: Dec. 5, 2013

(65) Prior Publication Data
US 2015/0160135 A1   Jun. 11, 2015

(30) Foreign Application Priority Data

Jun. 1, 2012 (NL) .................................... 1039638
Mar. 12, 2013 (NL) .................................... 1040089

(51) Int. Cl.
| | | |
|---|---|---|
| G01N 1/00 | (2006.01) | |
| G01N 21/64 | (2006.01) | |
| B01L 3/00 | (2006.01) | |
| B01D 61/14 | (2006.01) | |
| B01D 67/00 | (2006.01) | |

(Continued)

(52) U.S. Cl.
CPC ......... *G01N 21/6486* (2013.01); *B01D 61/14* (2013.01); *B01D 63/088* (2013.01); *B01D 67/0062* (2013.01); *B01D 71/02* (2013.01); *B01L 3/50255* (2013.01); *B01L 2300/069* (2013.01); *B01L 2300/0819* (2013.01); *B01L 2300/0829* (2013.01); *B01L 2300/0851* (2013.01); *B01L 2300/0893* (2013.01);
(Continued)

(58) Field of Classification Search
None
See application file for complete search history.

(56) References Cited

U.S. PATENT DOCUMENTS

2006/0252044 A1* 11/2006 Okumura ............ B01L 3/50255
435/6.11

FOREIGN PATENT DOCUMENTS

WO   WO 2011/011350   * 1/2011 ................ B01L 3/00

* cited by examiner

*Primary Examiner* — Robert Xu
(74) *Attorney, Agent, or Firm* — Joseph F. Aceto, Esq.

(57) ABSTRACT

A micro well plate is described for capturing and distributing single cells in individual wells is described, wherein at least one individual well is provided with a bottom plate having at least one pore to pass sample liquid, such that if one object or cell of interest is collected on the bottom plate of the well, the sample flow rate through that particular well is significantly reduced, minimizing the possibility that multiple cells or objects of interest entering the same well. The presented invention is particularly suited for obtaining single cells and/or microorganisms suspended in fluid samples for subsequent detailed interrogation.

17 Claims, 17 Drawing Sheets

(51) Int. Cl.
  *B01D 63/08* (2006.01)
  *B01D 71/02* (2006.01)
  *G01N 1/28* (2006.01)
(52) U.S. Cl.
  CPC .............. *B01L 2400/0406* (2013.01); *B01L 2400/0487* (2013.01); *G01N 2001/288* (2013.01)

Figure 3, panel A
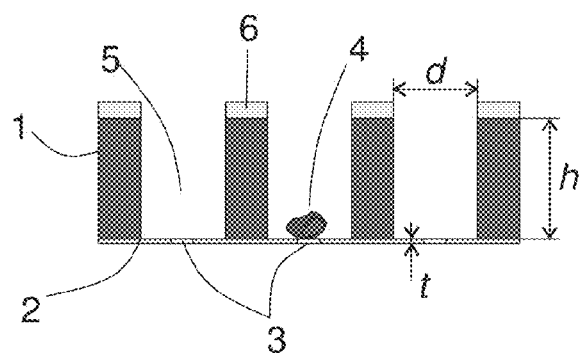
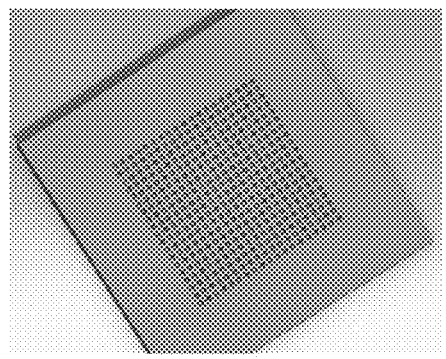
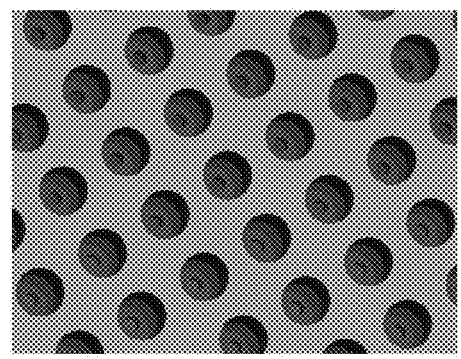
Panel B                             Panel C Panel A Panel B Panel C Panel D Panel A  Panel B  Panel C  Panel D Panel A             Panel B Panel A  Panel B  Panel C

Figure 21
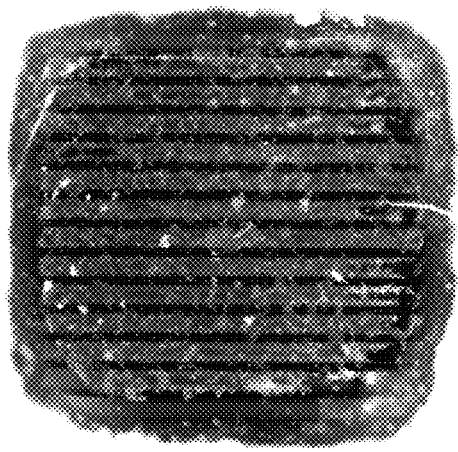 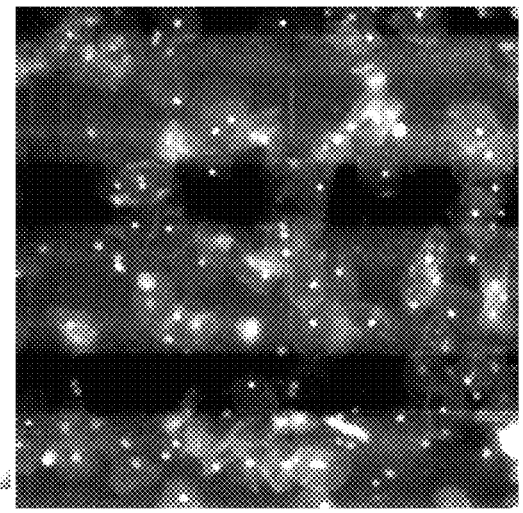
Panel A                    Panel B
Figure 22
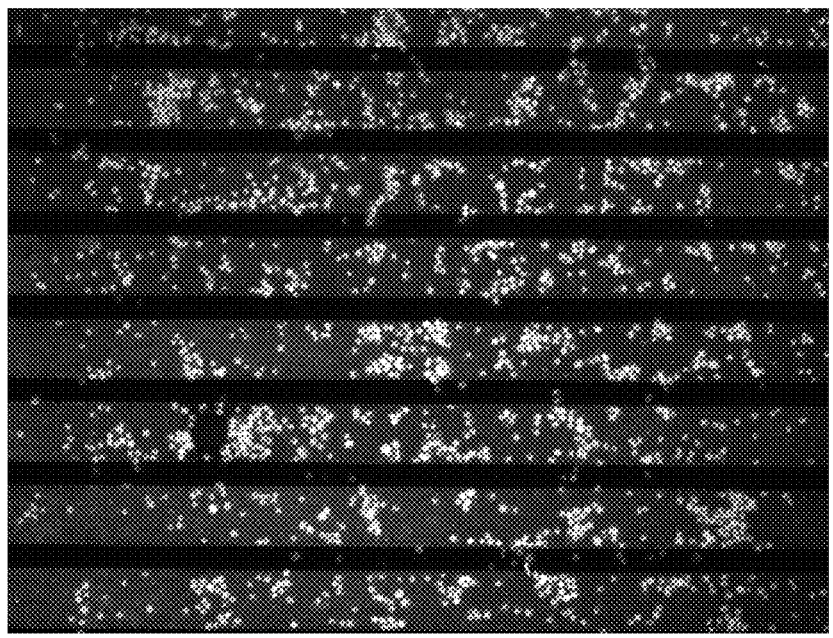

Panel A    Panel B

Panel A                               Panel B

Figure 27
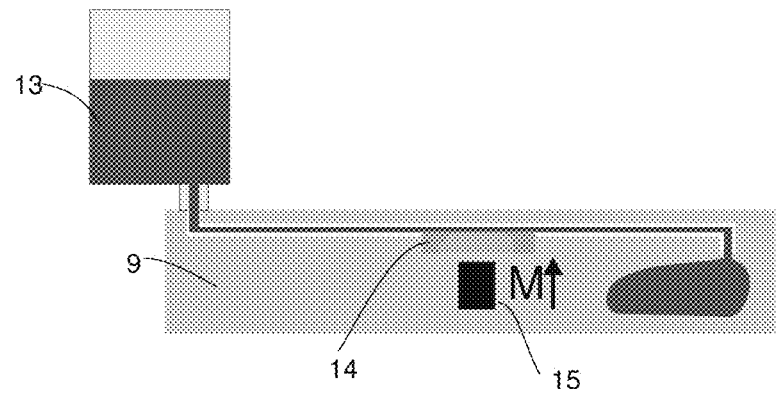
Panel A
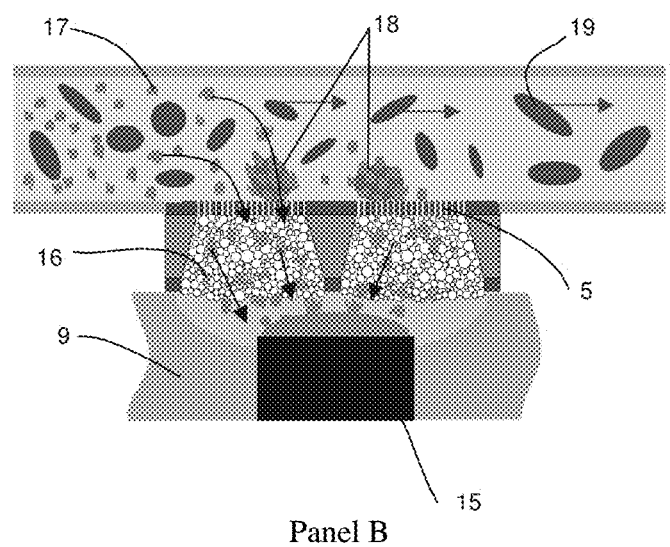
Panel B
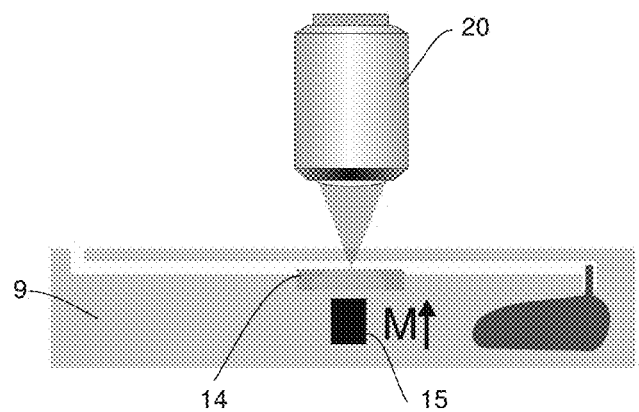
Panel C

MICROSIEVE DIAGNOSTIC DEVICE IN THE ISOLATION AND ANALYSIS OF SINGLE CELLS

CROSS-REFERENCE TO RELATED APPLICATION

This application is the national stage of International Application No. PCT/NL2013/050389, filed 29 May 2013, which claims the benefit of NL Provisional Application No. 1040089, filed 12 Mar. 2013, now expired, and NL Provisional Application No. 1039638, filed 1 Jun. 2012, now expired.

BACKGROUND

Field of Invention

The present invention relates generally to a simple and low cost diagnostic device for single cell separation and analysis. More specifically, the present invention relates to a microfiltration platform having a well-defined microsieve capable of separating and capturing target cells from a fluid sample for rapid interrogation in assessing cell status or diagnosing disease.

Description of Related Art

Single cell technologies are of extreme importance when only very few events are present in a sample. Examples of these are bacteria in bodily fluids and circulation tumor cells (CTC) in blood. By collecting these single events and subsequently perform analysis on the collected events such as analyzing DNA mutations and RNA/protein expression at a single cell level, a signature for these events can be established leading to a more specific treatment, development of new treatments and understanding of the underlying biological processes.

One common method to isolate cells for single cell analysis is by mechanically separating the cells into wells. Depending on the intended application a microwell device can be designed in numerous ways and with numerous different materials. Well-shaped structures of 10 and 20 μm in diameter have been fabricated using PDMS stamping of PEG poly(ethylene glycol) onto silicon substrates (Suh et al., 2004), and polystyrene substrates (Dusseiller et al., 2005). Mid-sized wells have been fabricated by surface engineered PEG on glass, creating arrays for improved optical cell imaging with wells capable of harboring more than one cell, such as 30×30 μm (Revzin, 2003) or 15×15 μm (Revzin et al., 2005) wells.

Suspensions of single cells are normally seeded manually into microwells, and the cells are randomly positioned in the wells by gravitation/sedimentation. To minimize the chance of having multiple cells within a single well, cell suspensions are diluted, causing a low percentage of wells actually filled. Other methods for seeding single cells into individual wells require wells with a volume that can only hold a single cell, eliminating the ability to add additional reagent to individual wells.

Thus the application of these designs in diagnostics is severally limited due, in part, because the remaining cells outside the well are flushed away, sometimes followed by another round of cell loading to increase the final number of captured cells. In cases where only a limited number of events (or cells) are present, as for example in the analysis of CTC, it would be detrimental to have cells outside the wells where they are flushed away.

Larger wells require micromanipulation to retrieve the cells from the wells. An example of cell retrieval from smaller cell-sized wells using micromanipulation was demonstrated by Tokimitsu et al., 2007. In general, cell retrieval and/or removal are important aspect for microwell chip design. However many single-cell micro-chips are designed to provide analysis with a continuous flow across the chip without the possibility for the investigator retrieving cells or clones to further analyze. Techniques for retrieval and manipulation of cells are very important, since sample screening often involves only a few cells worthy of further detailed analysis.

Filtration membranes in a microfiltration platform provide a means for capturing target events within a sample. Critical factors that determine a microfiltration platform in a diagnostic device are membrane composition and fluidic pathway design for liquid and sample manipulation. It is known that membrane filters are an indispensable necessity in the field of diagnostics such as in sample preparations for scanning electron micrographs where track etched membranes are used or in determining the number and type of micro-organisms and/or cells in a given sample.

Micromachined microsieves have been described as a type of microfiltration membrane comprising a supporting substrate and a thin membrane layer with precisely etched pores which are mechanically stable and have high pressure strength at a thickness of only a few hundred nanometers. Thus, these microsieves are useful for diagnostic applications and have been incorporated, in part, in the present invention. Prior to the present invention only conventional filtration membranes were used. With respect to current filtration membranes microsieves have several specific advantages including, in part, a very low flow resistance, regular and precise pore geometry and an optically flat surface. The sample liquid is filtered through the microsieve which has a low flow resistance allowing for high flow rates which results in the collection of cells and microorganisms in a relatively short time. The optically flat surface enables a single image of the microsieve surface to be acquired without the need to refocus on different locations across the microsieve. Furthermore the microsieve is chemically inert and has no disadvantageous fluorescence back light scattering which further improves the staining and detection of micro-organisms for imaging through a fluorescence microscope.

Polymeric materials currently used in conventional filtration membranes are not well suited as microsieves. Membranes formed with these materials are characterized by relatively small values for Young's Modulus and/or a low yield strength and so are not suitable for fabricating into microsieves.

Another problem associated with the use of current filtration membranes to capture cells or particles from fluids is the inability of the sample fluid to easily start flowing through the openings in a microsieve membrane. Most micromachined filters have an inorganic membrane layer such as silicon nitride or silicon oxide with water contact angles above 30° and in time can even rise above 60°. At a pore size of 1 um, fluid flow through the microsieve can then only be induced at pressures above 100 mbar. A normal procedure to reduce this pressure is to create hydrophilic hydroxyl groups with oxygen plasma at the membrane surface just before use. Another normal procedure to reduce this pressure is to pre-wet the back side of the microsieve with an additional fluid. However for many applications, especially for in vitro diagnostic point of care analysis, the pressure needs to be reduced to zero. At zero pressure the fluid will flow through the filter without the need of applying pressure. Without the need to pre-wet or pressurize the fluid, the microsieves become usable in a wide range of applications where they were rather unpractical before.

Accordingly with these limitations in the prior art, there exists a medical need to develop a filtration platform which incorporates the micromachined microsieves described herein,

SUMMARY

The present invention resolves the limitations of the prior art by incorporating characteristics described herein using a microsieve diagnostic device for capturing and distributing single cells from a fluid sample. A micromachined microsieve and absorbing pad provide a filtration membrane system for capturing individual cells. Fluidic pathways are available for transport of sample fluid, reagents, and waste to and from the captured cells. The device further considers subsequent interrogation of captured cells using fluorescence spectroscopy or other techniques known in the art.

One embodiment of the present invention is to provide microfiltration membranes which allow the passage of fluids at zero pressure towards the absorbing pad, referred to as wettable sieves. The present invention provides wettable microsieves where upon contact with the sample allows the passage of the sample through the wettable microsieves, thus creating immuno activated wettable microsieves that enhance the capture of specific cell populations. The construction, design and use of these immuno activated wettable microsieves in a variety of applications are embodied in the present invention and described in detail herein.

Still another embodiment of the present invention provides a diagnostic device comprising a first element with at least one filtration membrane, a second element with at least one absorbing pad to absorb sample fluid while leaving objects of interest behind on the filtration membrane.

The second element optionally contains multiple compartments that can contain absorbing bodies and reactants contained in pouches, pads or other fluid holding devices or other necessities to enable the analysis of objects or cells retained on the filtration membrane.

These embodiments support diagnostic devices that not only enables easy transport of sample fluid from the filtration membrane towards the absorbing pad, but also includes a means for enabling the transport of reagents towards the object(s) or cell(s) retained on the membrane for subsequent analysis, identification, differentiation and/or counting of the sample fluid object(s) or cell(s) retained on the filtration membrane. For example, one type of subsequent analysis is to differentiate the objects or cells collected onto the sieve by fluorescence microscopy. In this method the reagents containing fluorescence labels are transported towards the captured object(s) or cell(s) to allow labeling for fluroescence imaging.

Therefore one preferred embodiment of the present invention comprises a device having at least one reagent reservoir and a fluidic pathway for transporting the fluid from the reservoir towards the filtration membrane, herewith enabling analysis of sample fluid components (i.e. objects or cells) retained on the filtration membrane by fluorescence microscopy.

The fluid contained in the reagent reservoir optionally comprises reactants for selective recovery or detection of sample object(s) or cell(s) retained on the filtration membrane. The reactants can be fluorescent labels or antibodies that are specific for the retained species. They may also include specific markers, such as colloidal particles, micelles, enzymes, chromophores, beads, radioactive labels, fluorophores or mixtures thereof to facilitate the direct or indirect detection of the intended species.

In still another preferred embodiment, a diagnostic device is described having a first element with a movable filtration membrane with respect to the second element having an absorbing pad. Movement by either rotation or translation provides a switching means to stop fluid transport across the filtration membrane from the first element towards the second or from the second element towards the first element.

In still another embodiment, the present invention provides applications of the diagnostic device in the capture of specific cells or microorganisms. It is a further object of the present invention to provide a micromachined microsieve platform and associated methods use in specific applications. For example, but not limiting, microsieves coated with adhesion molecules used in targeting specific cells associated with these molecules.

Another preferred embodiment incorporates a microwell plate for capturing and distributing single cells in individual wells, comprising a micro well plate having micro wells with a bottom plate, a sample supply side and a sample discharge side, wherein at least one individual well is provided with a bottom plate having at least one pore to pass sample liquid from the supply side to the discharge side. The object or cell of interest is collected on the bottom plate of the well while the sample flow rate through that particular well is reduced to minimize the possibility of multiple cells or other objects of interest entering the same well. A single cell or object of interest is then able to close at least one pore of the well bottom plate, promoting single cell capture and allowing the addition of reagents to individual wells. This microwell plate is easily combined with another platform for further interrogation of the specific cell, either by applying methods such as, but not limited to, PCR, RT-PCR, FISH or comparable DNA and RNA analysis, making this well suited for obtaining single cells and/or microorganisms suspended in fluid samples. The invention is well suited for use in many disciplines including, but not limited to, healthcare, life science and medical treatment applications as well as food safety and food technology.

Another embodiment of the present invention provides a method of manufacture for the microsieves and the device.

Still another embodiment of the present invention provides methods for the use of the microfiltration diagnostic device in disease.

BRIEF DESCRIPTION OF THE FIGURES

FIG. 3 Panel A is diagram of a cross-section of a microwell having dimensions d and h with a single cell, 4, closing one of the pores. Panel B is an image of a microsieve in a microwell format with microwells arranged as a single square in the center of the microsieve. Panel C depicts a magnified portion of the microsieve with each microwell having a single pore capable of being occluded by a single cell.

FIG. 21 shows a fluorescent image of cells isolated from urine and stained with Acridine Orange. Panel A: image of the entire surface of the microsieve, magnification 4×. Panel B: a further magnification showing only a portion of the entire microsieve.

FIG. 22 shows a fluorescent image of SKBR-3 cells on a microsieve having a pore size of 5 microns. Cells are labeled with Acridine Orange.

DETAILED DESCRIPTION OF INVENTION

Figure 1:
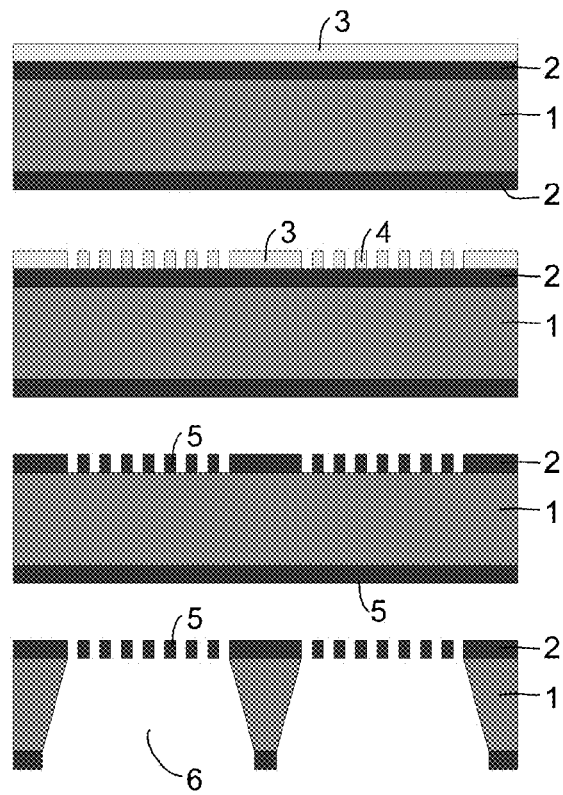
FIG. 1 shows the layers and their structure in the manufacture of the microsieve.

The microwells described in the present invention provide an alternative system to the continuous flow paradigm currently used which has limited ability for further detailed analysis. The present invention utilizes a microwell plate for capturing and distributing single cells in individual microwells, comprising a microwell plate having microwells with a bottom plate, a sample supply side and a sample discharge side, wherein at least one individual well is provided with a bottom plate having at least one pore to pass sample liquid from the supply side to the discharge side. If one object or cell of interest is collected on the bottom plate of the well, the sample flow rate through that particular well becomes greatly reduced, minimizing the possibility that multiple cells or objects of interest can enter the same well. A single cell or object of interest should be able to close at least one pore of the well bottom plate, allowing for single cell capture. The base of every well is therefore provided with a single pore or a set of pores. When a fluidic sample with the objects of interest are applied to the micro wells, the fluid will enter the wells at the supply side and will leave the wells through the pores at the bottom of the well at the sample discharge side. Hydrodynamic forces take the objects of interest with the flow to be collected at the bottom of the well on the pores which have a dimension smaller than the objects, thus reducing or stopping the sample flow rate through that particular well and minimizing the possibility that multiple cells or objects of interest can enter the same well in a later time. A single cell or object of interest is able to close most of the pores present in the well bottom plate. One preferred embodiment has, in part, a bottom plate with only a single pore and having a size smaller or comparable to the cell or object of interest. The advantage of a single pore is that the well is immediately totally closed after the capture of a single cell preventing other cells in the sample fluid to enter the well. Also with respect to the flow, flux through one pore with size d is higher than the flux through N pores with size d/N, and this enables a relatively fast flow of the sample fluid.

Structurally, thin bottom plates with pores are preferred and can be manufactured by a means similar to micromachined microsieves, comprising a supporting silicon substrate and a thin ceramic membrane layer with precisely etched pores. In this way mechanically stable and thin membranes with high pressure strength are made, even when the membrane has a thickness of only a few hundred nanometers. The design and dimensions of the microwells have a support structure similar to the microsieve, but with an open support structure to form the microwell plate. The microwells and microsieves described in the present invention have a number of specific advantages such as a very low flow resistance, regular and precise pore geometry and an optically flat surface.

Optimally, the bottom plate of the microwell near the pores has a thickness less than ten times and preferably less than three times the diameter of the pores, herewith enabling a high sample fluid flow through the pores. Furthermore the microwell plate is chemically inert and is devoid of any fluorescence back light scattering, herewith avoiding unwanted chemical reactions and facilitating the staining and detection of targeted objects or cells with a fluorescence microscope. The multiple or single pore design in a bottom plate are centered in the middle of the well, in order to promote microscopic observation. After the capture of a single cell in a microwell, the remaining pores are optionally sealed through various methods to allow a chemical or biological reaction between the collected object and an added reagent without cross interference between different microwells. The pores in the bottom of the microwells can be closed by using many different methods which can incorporate the use plastic foil or plate, a thin fixating material or the deposition of a hydrophobic agent. Examples of reagents that can be added in a chemical or biological reaction can be, but not limited to, e.g. fluorescence labels, PCR reagents, DNA amplification reagents or reagents that can lyse the cells. After completion of the reaction the fluid can be removed from each individual microwell by using micro-pipetting or by opening the pores at the bottom of the well.

Another aspect of the microwell design focuses on the retrieval of collected objects of interest. Micropipetting the single cells from individual microwells is possible, but requires a skilled operator and has the potential of large loss cells. Alternatively as a further embodiment of the present invention, a method is described which has been developed to remove (or punch-out) the bottom of a pre-selected well which has a captured object. After collection of the punch-out bottom, it is easily transferred to a microscope slide, a tube, a sample cup, or the well of a standard PCR plate, allowing the use of standard commercially available reagents and platforms to further interrogate the collected single objects or cells. To enable the removal of the bottom plate of an individual well, a bottom plate from a ceramic material such as silicon nitride with a thickness between 200 nm and 2 micrometer is most preferred.

Manufacture and Design

Figure 2:
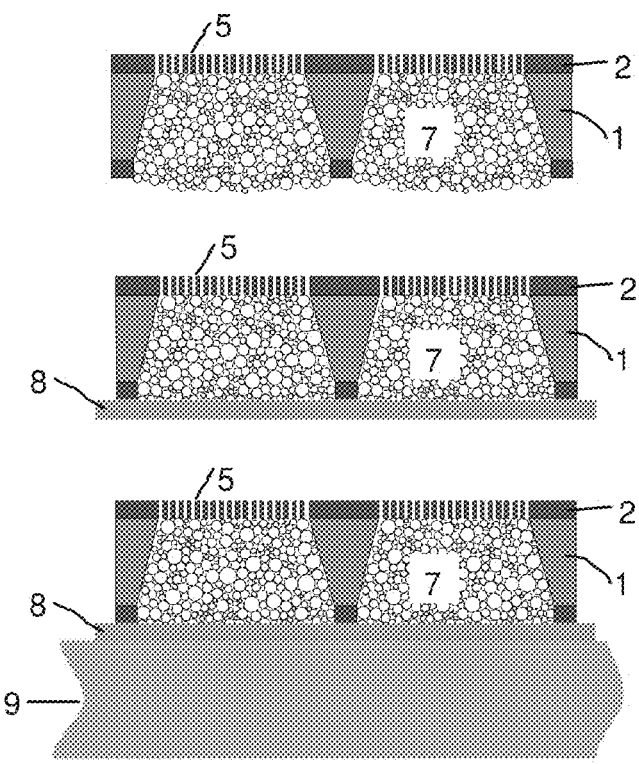
FIG. 2 shows a microsieve where the cavities are filled with a porous material to enable capillary flow.

The manufacturing process for the microsieve filled with porous material is described herein and represented in FIG. 1. On a monocrystalline silicon wafer, 1, a silicon nitride membrane is made with openings having a pore size of 3.5 micrometer. The silicon nitride layer, 2, has a thickness of 900 nanometers and is low stress silicon nitride deposited on a 750 μm thick polished silicon wafer, 1, by means of a low pressure chemical deposition process commonly used in the art. Next a photoresist layer, 3, is formed by spin coating. This layer is patterned with pores, 4, having a diameter of 3.5 micrometer by exposing it to UV light through a photo mask. The pattern in the photosensitive layer 3,4 is transferred into the silicon nitride membrane, 5, by means of RIE (Reactive Ion Etching) and pores, 5, in the membrane are formed. Large cavities, 6, are anisotropically etched in the monocrystalline silicon substrate, 1. For other substrates other micromachining methods can be used to form the cavities in the substrate, such as molding, electroplating, lasering, etc. In order to facilitate the flowing of liquid through the microsieve pores, 5, a porous absorbing material, 7, has been deposited in the cavities, 6, after the forming process of the cavities. FIG. 2 shows the absorbing material, 7, is in close contact with the membrane 2,5. Close contact means that the nearest distance of the absorbing material and at least one membrane pore is in the order (≤10×) of the pore diameter, herewith enabling capillary contact and flow. An advantage is that the manufacturing process of the microsieve with the cavities is uncoupled from the process of filling the cavities of the microsieve with the porous material, enabling good process control for two distinct production steps. In the figure the whole microcavity is filled with a porous material.

Preferably the porous material has a mean pore size between 10 nanometers and 10 micrometers. When smaller than 10 nanometers, the pore size will excessively restrict the capillary flow, conversely when larger than 10 micrometer the pore size will not induce capillary flow. One example is a porous material comprising an aggregate of silica particles having a mean particle size of 5 micrometer which is deposited by applying a 3% solution via the back side of the wafer. The silica particles can be fixated with different techniques, such as surface modification, gelation, sintering etc. Of course many other methods can be employed for filling the cavities with a porous material, such as phase separation, phase inversion, template leaching, sintering of microbeads etc.

In addition to the porous material a nano-porous thin hydrophilic material layer along the walls of cavity and membrane can be applied. Fluid molecules can enter this layer herewith increasing the wettability of the filtration membrane and increasing the flow rate of the sample fluid passing through the filtration membrane. Depending on the application and design of the filtration membrane having a porous material, only a hydrophilic layer or a combination of these two can be used to obtain the right filtration membrane characteristics.

Further considered are the cavities containing the porous material, 7, which can be attached to a porous covering layer, 8, strengthening the back side of the microsieve. It will also facilitate further transport of liquid if this porous covering layer, 8, is attached to a large absorbing porous body, 9, that is capable of absorbing all the transported liquid by capillary action. Depending on the choice of materials for the porous material, 7 and the large absorbing porous body, 9, porous covering layer, 8, can be omitted.

FIG. 3, panel A depicts the design of the microwell plate. In a silicon wafer, 1, with a thickness (h) of 380 micrometers containing large cavities in the form of wells, 5, made through any appropriate dry or wet etching method known in the art. On the bottom of the wells, 5, a silicon nitride membrane, 2, is provided with one or a multiple number of pores, 3, having a diameter between 0.2 and 20 micrometers, typically with a size smaller that the objects of interest. The silicon nitride layer 2 is low stress silicon nitride with a thickness (t) between of 0.2 and 2 micrometer.

The large wells, 5, are facing towards the sample fluid and can be used to capture target objects, cells, or microorganisms and further can be used as a bio reagent chamber. FIG. 3, panel B presents a microwell plate with round cavities 5 having a diameter (d) of 100 microns in a 3×3 mm$^2$ area. A closer view of the wells with single pores is presented in FIG. 1, panel C. The thickness (t) of the bottom plate is smaller than the diameter of the pores, 3, to achieve a low flow resistance. Here each cavity, 5, has only a single pore. When a cell, 4, enters the cavity it will land onto the pore, hereby enhancing the flow resistance and forcing other cells to enter a different cavity. In this way the chance that multiple cells are present in a single cavity is considerably decreased. This microwell plate is very well suited for the analysis of single cells, 4, that are present at very low densities (typically a few per milliliter). Examples are tumor cells that are present in bodily fluids, such as pleural, spinal and urine fluid. Amongst the tumor cells other, non-malignant cells are present in these fluids. To be able to analyze the DNA of the individual tumor cells it is important that their DNA is not mixed with DNA of other cells. As such the cell content from each of the collected cells needs to be kept isolated to be able to analyze the DNA constituents of individual cells. Additionally the top of cavity walls can be supplied with an additional hydrophobic layer, 6, as an extra measure to prevent mixing of the contents of individual wells. The hydrophobic layer, 6, can be applied by applying silane with a hydrophobic end group such as an alkane to a pretreated silicon nitride layer or using any other method known in the art.

Seeding and Labeling/Staining of Captured Cells

Figure 4:
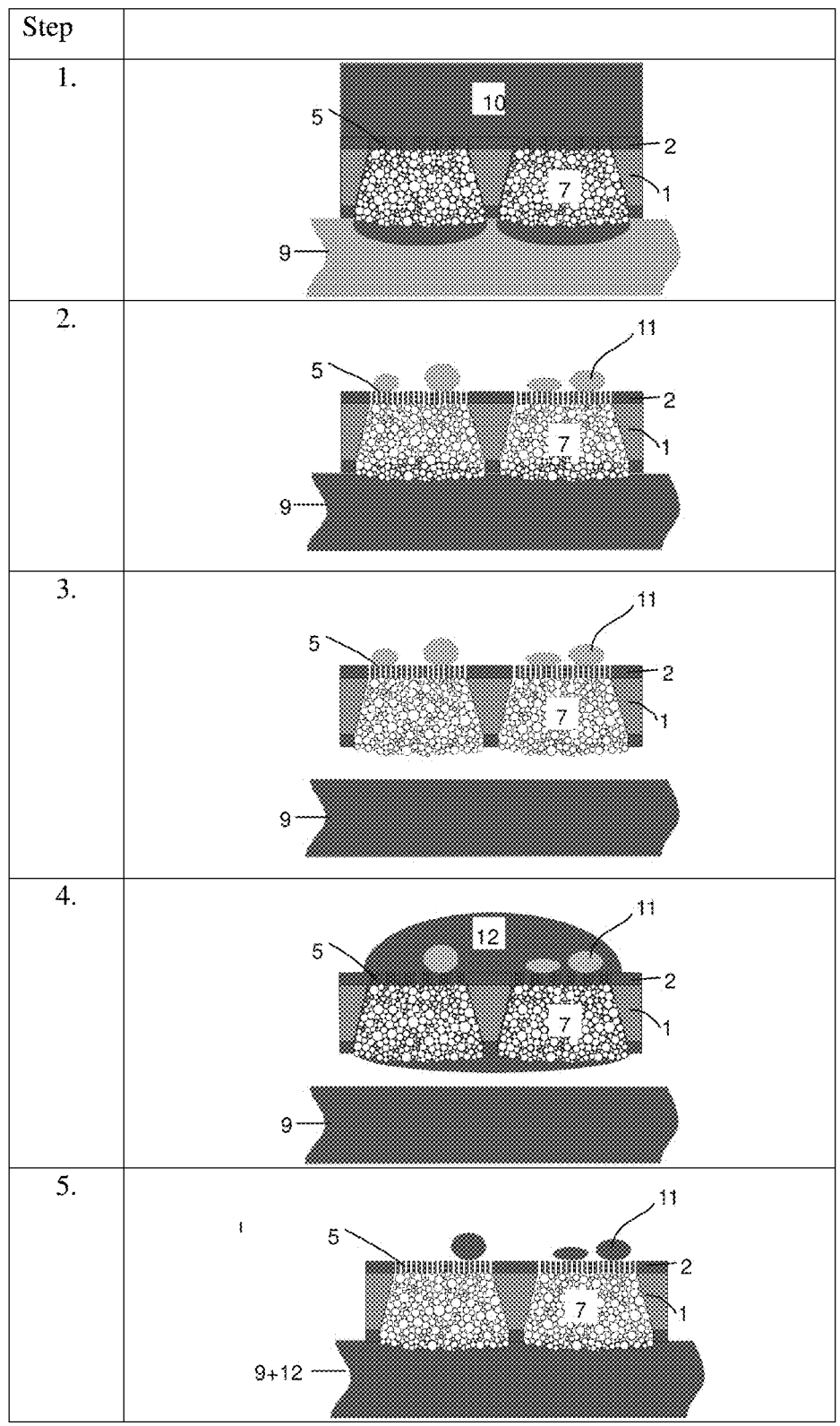
FIG. 4 represents the steps in the staining process of filtered objects of interest by making and breaking contact between the microsieve and the absorbing body.

The general procedure for seeding and staining cell captured on the microsieves is schematically illustrated in FIG. 4, steps 1 to 5. Normally a relatively large amount of reagent is required for staining cells retained on the filter. To avoid this requirement, the continuity between the absorbing body, 9, and the microsieve can be restricted. Any contact between the absorbing body, 9, below the porous material, 7, of the microsieve will cause fluid above the wettable microsieve to move through the pores of the microsieve and absorbed through porous layer, 8, by the absorbing body, 9. When continuity is lost, the fluid cannot move through of the porous material, 7, and will remain above the absorbing body, 9.

Step 1: Sample fluid containing target cells, 10, is put onto the microsieve, shown in contact with the absorbing body, 9.
Step 2: After the sample has passed through the wettable sieve the filtered events/cells, 11, remain on top of the microsieve.
Step 3: The wettable sieve and the absorbing body, 9, are detached from each other.
Step 4: Reagent or reagents for labeling and/or staining, 12, are put on top of the wettable microsieve. Without the continuity between the microsieve and the absorbing body, 9, the reagents remain on top of the microsieve.
Step 5: To remove reagent after incubating with filtered events/cells, the wettable microsieve is brought in contact again with the absorbing body, 9, resulting in the movement of excess reagents, 12, into the absorbing body, 9. Further washing is easily accomplished by repeating Steps 3-4-5 with a washing solution. Multiple reagent additions and washing steps are also considered if required.

Figure 5:
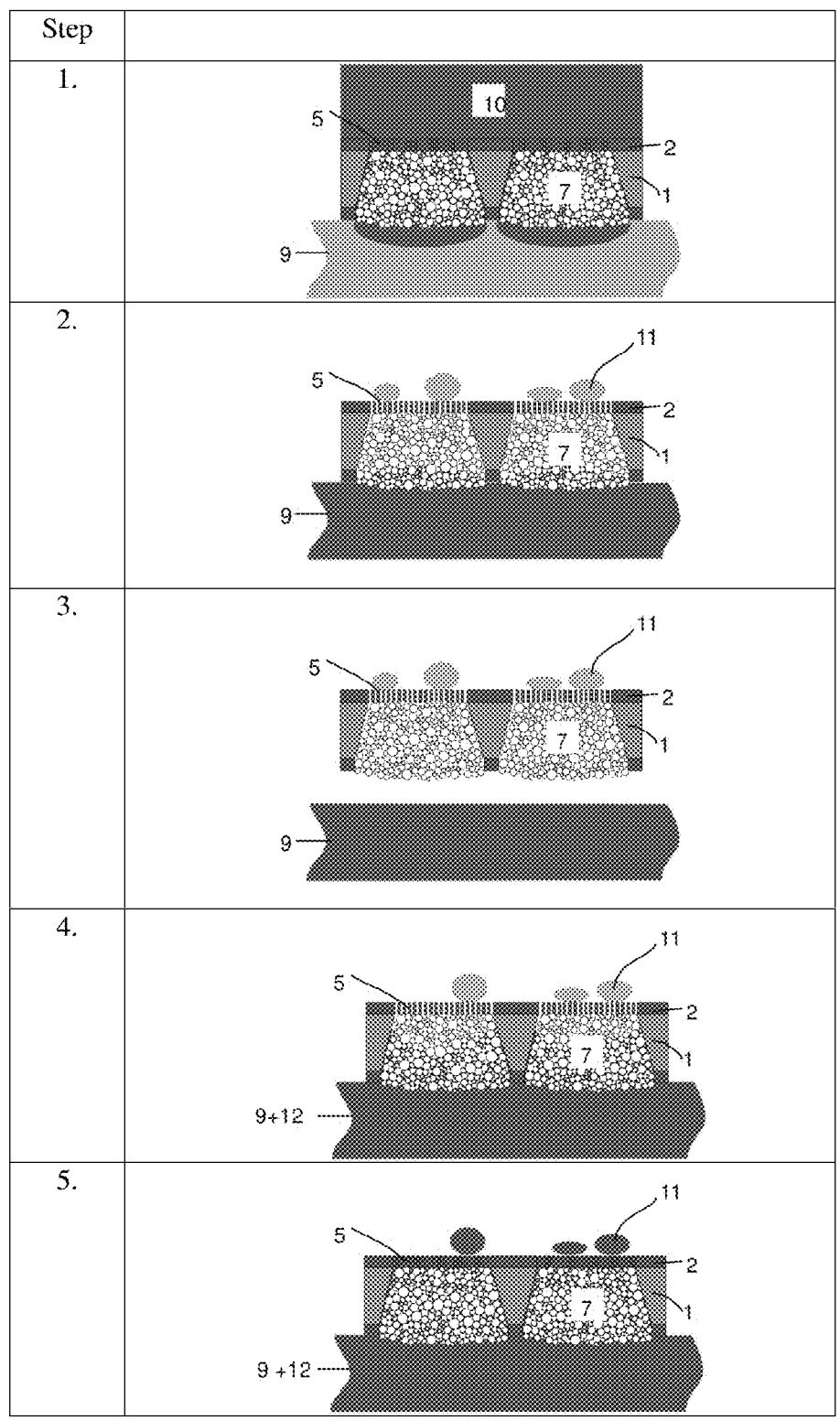
FIG. 5 represents the steps in the filtering process followed by the staining of cells with the movement of reagents from a reservoir towards the membrane.

For Point-of-Care applications it is important that the device and method are operator friendly. For such applications the reagents can be prepared in disposable chambers. For example pre-loading the absorbing body, 9, with the reagents, 12, needed to stain the cells or microorganisms is accomplished as illustrated in FIG. 5, step 1 to 5.

Step 1: Sample fluid containing target cells, 10, is put onto the microsieve, shown in contact with the absorbing body, 9.
Step 2: After the sample has passed through the wettable sieve the filtered events/cells, 11, remain on top of the microsieve.
Step 3: The wettable sieve and the absorbing body, 9, are detached from each other.
Step 4: The absorbing body, 9, now contains the sample fluid, 12, is replaced by an absorbing body that is pre-loaded with reagents, 9+12. Instead of replacing the absorbing body, 9, with a pre-loaded body it is also possible to transfer the sieve to the pre-loaded body, 9+12. The reagents will move out of the absorbing body, 9+12, by capillary forces, into the porous material, 7, of the wettable sieve and towards the filtered objects/cells, 11. In one embodiment the absorbing body is divided in different sections where each section is connected to a different area of the microsieve membrane
Step 5: The filtered objects/cells, 11, reacts with the reagents. To remove excess reagent after reacting with filtered events/cells, the wettable microsieve is brought into contact with an empty absorbing body, 9.

Figure 6:
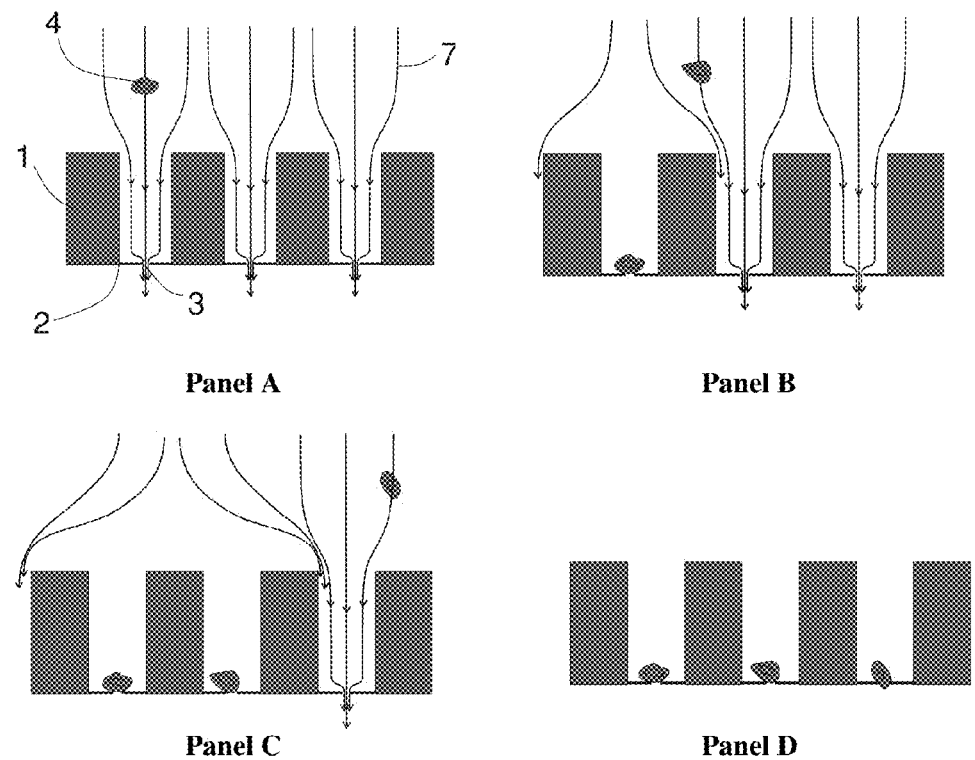
FIG. 6 diagrams the seeding of single cells within individual microwells. Panel A shows the initial entry of the target cell into the microwell. Panel B shows the same microwell with the flow diverted because of the occluded pore. Eventually more cells block the pores of the individual microwells as shown in Panel C. Panel D shows all the micro wells containing the target cell.
Figure 7:
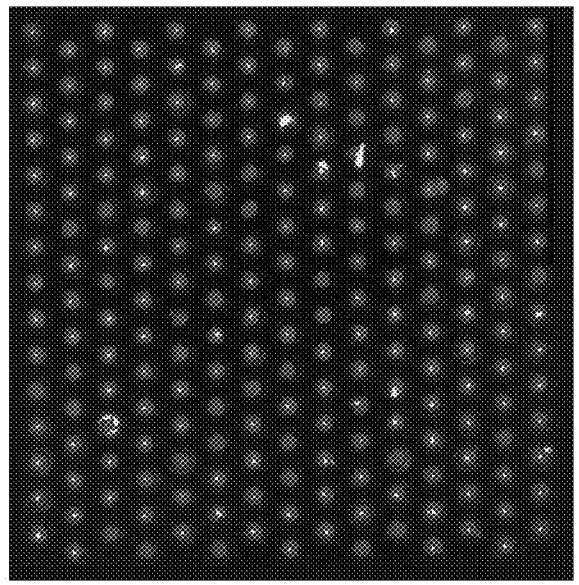
FIG. 7 is an image of single cells captured within each individual well. Each well contains exactly one pore with a diameter of 5 microns. Cells are SKBR-3 cells fluorescently labeled with Cytotracker orange.
Figure 8:
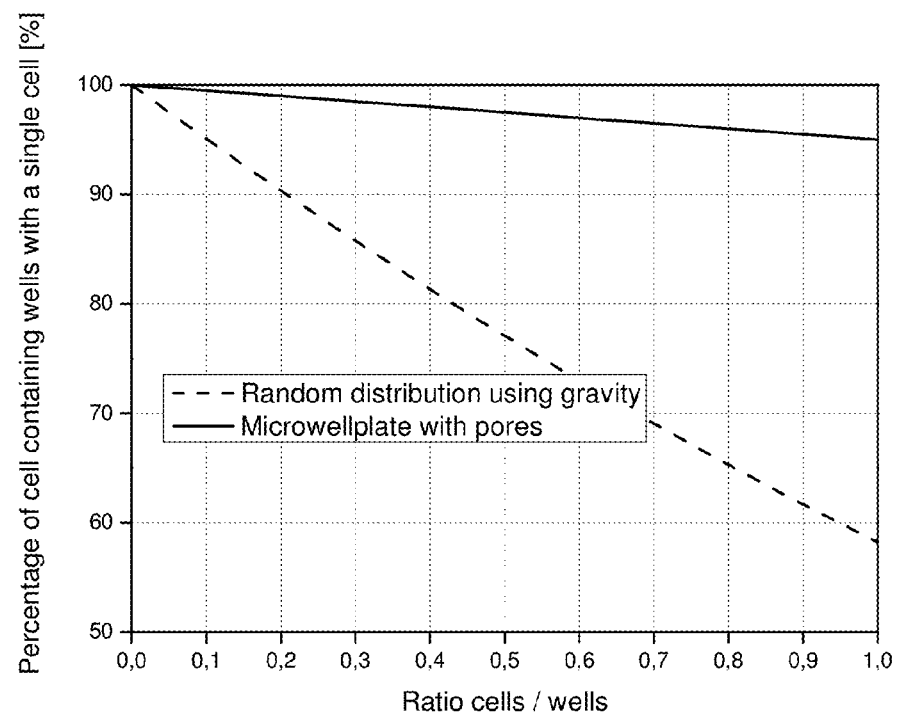
FIG. 8 shows a graph comparing the percentage of cell containing wells to the ratio of cell number per available microwells when randomly distributed across collection wells (dotted line) compared to a microwell plate having individual pores in each well (solid line).

A schematic illustration for seeding single cells into individual wells in the microwell platform is shown in FIG. 6. A sample fluid containing target events/cells, in this case a sample fluid with cells, 4, is added to the sample supply side, corresponding to the side with the large cavities in the microsieve. The fluid flows in the wells and flows out of the well through a single pore at the bottom plate of the membrane. Each well has a single pore with dimensions smaller than the objects of interest. The objects of interest are dragged by flow and hydrodynamic forces into the well (FIG. 6, Panel A). As a result the objects of interest will land on the pore of a well significantly restricting or stopping the flow rate through the pores thereby minimizing the chance that a second object will enter the same well (FIG. 6 Panel B). This process continues as shown in FIG. 6, Panel C until all the sample fluid has passed through the wells. The end result is that the occupied well will contain one single cell (FIG. 6, Panel D). FIG. 7 shows a photograph of single cells seeded into individual wells. In this particular example SKBR-3 cells are fluorescently labeled with CytoTracker™ orange and distributed in a fluid (CytoTracker is a trademark of Molecular Probes, Inc., Eugene Oreg.). The number of available wells versus the number of cells is 1:0.95. As shown in the photograph, 96% of the wells that contain cells contain a single cell. The graph in FIG. 8 compares the percentage of cell containing wells that contain a single cell as a function of the ratio between the number of cells and the number of available wells using the seeding method described. The dotted line represents cells that only sink into the wells by gravity. The distribution of the number of cells per well by gravity follows a Poisson distribution, whereas the seeding method (solid line) results in a much higher percentage. At a ratio of cell/wells of 0.8 a seeding method that uses only gravity results in 65% of the wells having a single cell whereas the seeding method described results in 96% of the wells having a single cell, an increase of 31%.

Figure 9:
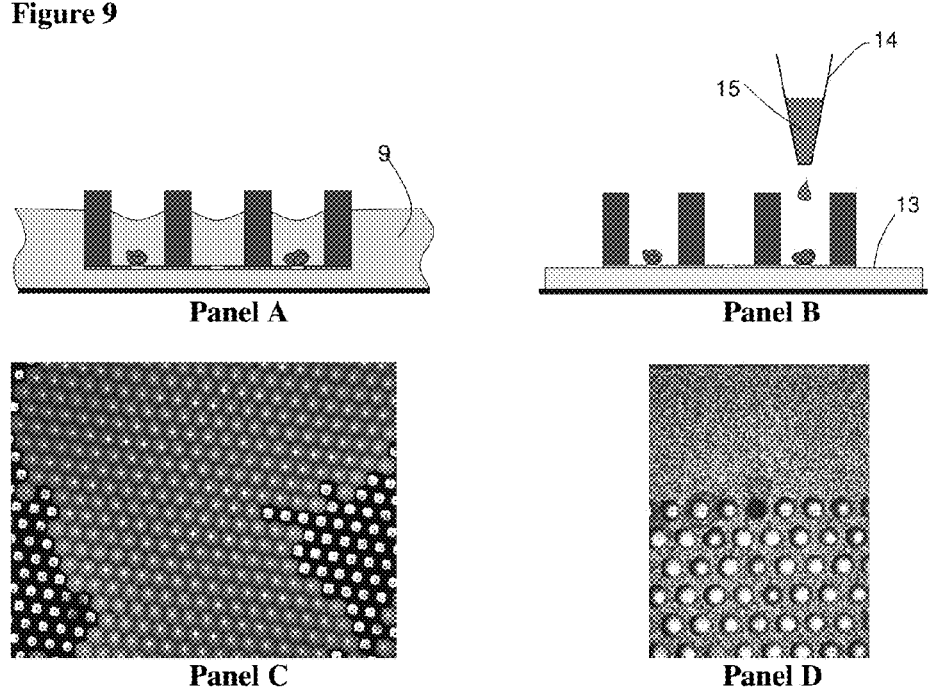
FIG. 9 depicts two techniques for adding reagents to microwells. In Panel A the membrane is submerged into the reagent. Panel B reagents are added directly by pipetting reagent into each microwell. Panel C is a photograph of the microsieve after submerging into reagent. Panel D shows the results of microwells filed by printer technologies.

The addition of reagents for labeling or staining is represented in FIG. 9. FIG. 9, panel A illustrates the process for filling wells with reagent by submerging the bottom plate with the pore into reagents, 9. The reagents are forced to move into the wells through the pores. FIG. 9, panel C shows a photograph of the wells filled with reagents using this process. At the time the image was acquired approximately 80% of the wells were filled with the reagents already. This method is most appropriate when the same reagents are added to all wells and cell lose is not acceptable.

Alternatives to submerging the perforated microwell plate into reagents, 9, involve micropipetting or printing reagents in individual wells, well by well. FIG. 9, panel B presents a schematic image of pipetting reagents, 14, using a micropipette, 15. To prevent the reagents from leaking through the pores, the pores are closed with a sealing sheet, 13, before the reagents are added.

Instead of using a micropipette, reagents can be printed in the wells using inkjet technology. The image in FIG. 9, panel D shows a well plate where one of the wells is filled with reagents using inkjet printing technology.

Interrogating Captured Cells

Figure 10:
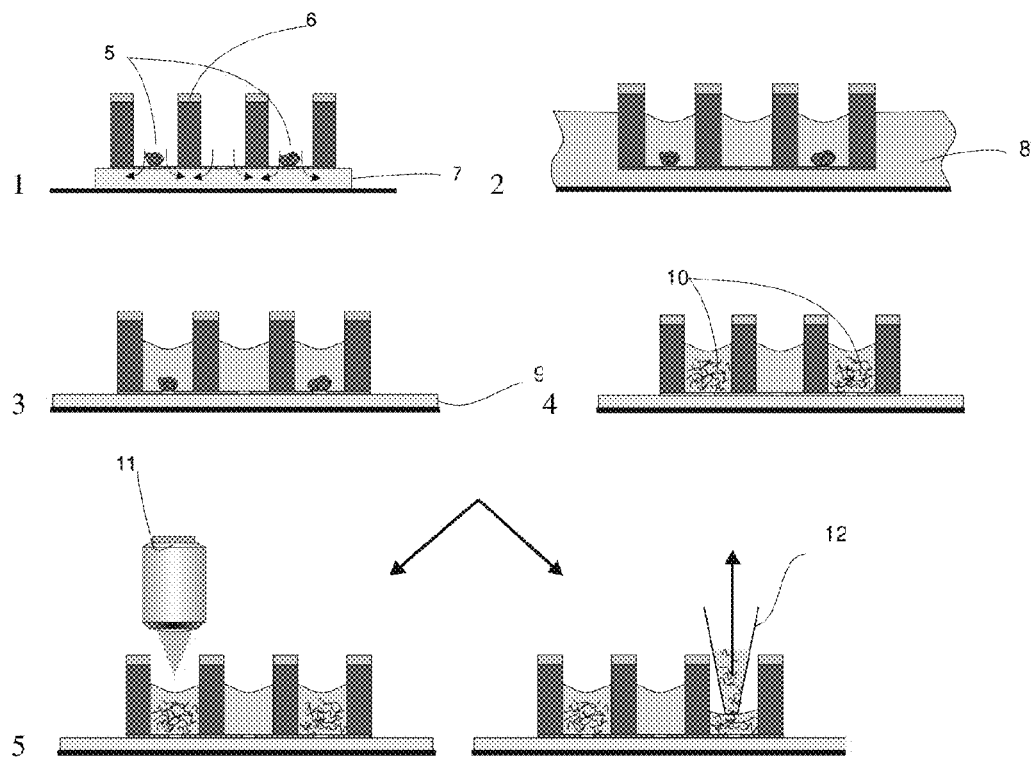
FIG. 10 shows the steps in processing and analyzing captured cells for DNA analysis.

As previously discussed, the present invention enables a detailed analysis of each individual cell after isolation and separation from the sample fluid. For example in the microwell plate, subsequent analysis after isolation and separation from the sample fluid may include DNA analysis of each individually captured cells. FIG. 10 diagrams a 5 step process incorporating fluorescence spectroscopy in an analysis of captured cells for three separate microwells.

Step 1: Cells, 5, are seeded onto a perforated microwell plate which is then brought into contact with an absorbing body, 7. The fluid sample passes through the microwell plate towards the absorbing body, 7, while leaving the cells, 5, behind on the pores. Next the cells are fluorescently labeled and fluorescence microscopy identifies the wells containing the cells of interest. The locations of the specific microwells are recorded for subsequent analysis after amplification of the DNA.

Step 2: The microwell plate is moved towards a compartment that contains the reagents for DNA amplification. In this example microwells containing pores at the bottom are dipped into the reagents, 8. The reagents, 8, will move through the pores towards the cells, filling all of the microwells.

Step 3: After the reagent volume has equilibrated within the microwells, the microwell plate is pressed onto a seal, 9. This prevents fluids from escaping through the pores while incubating. If needed for labeling, a series of reagents can be used with or without drying, washing, or fixation of the sample between each step.

Step 4: With the pores closed, the PCR reaction (or DNA amplification reaction cycle) amplifies DNA or DNA of interest. The amplified DNA, 10, stays inside the individual microwell of the captured cell. If needed in the assay, temperature can be cycled.

Step 5: Two options are possible. (A): During amplification a fluorescence label against a specific DNA sequence is incorporated in the amplification. In this case the presence of a specific sequence is detected using, for example, the fluorescence intensity where the fluorescence light is collected by an objective, 11, as used in Real Time PCR reactions. (B): The amplified DNA is transferred to another platform for further analysis, e.g. sequencing, using for example a pipette tip, 12, having dimension smaller than the diameter of a well.

Figure 11:
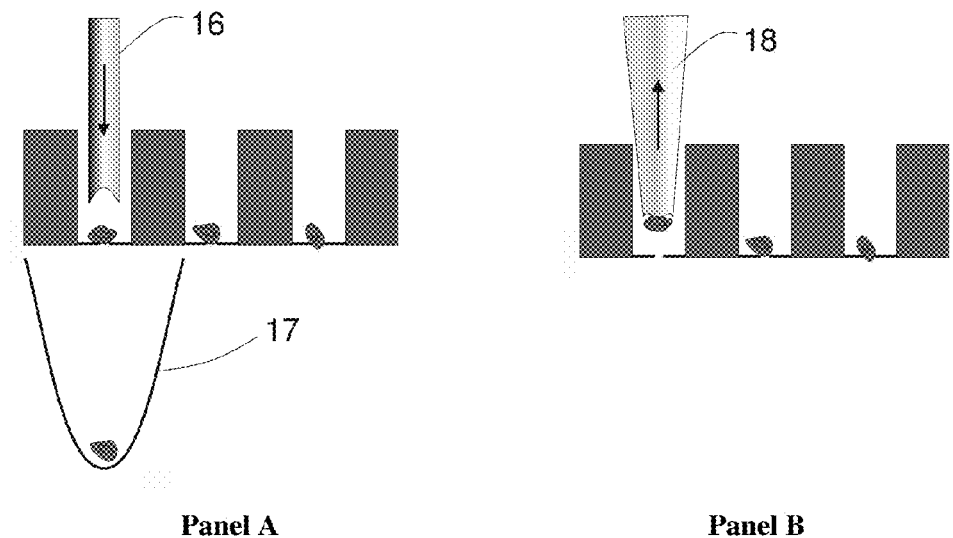
FIG. 11 shows two separate processes for retrieving a cell after capture. Panel A shows a punching process where the bottom of the microwell is punched out along with the captured cell and transferred to a reagent tube. Panel B depicts individual cells being removed by micropipetting.

FIG. 11 shows two different approaches for retrieving individual cells from their wells for subsequent analysis. FIG. 11, panel A illustrates a method requiring the removal of the whole bottom, including the collected cells, from the well by punching the bottom out. The bottom with a captured cell is punched, by a puncher, 16, into a reaction tube, 17, suitable for the next step in the analysis, e.g. in wells of a PCR well plate. Depending on the requirements, different materials for the puncher can be used such as stainless steel or glass pipettes. Removal of the whole bottom will only work for brittle, non-elastic materials. A silicon nitride bottom as used in this invention is very well suited.

Alternatively micropipettes can be used to remove the cell from the microwell as illustrated in FIG. 11, panel B. A small suction force is applied to the micropipette, 18, to hold the cells while being removed from the microwell.

Figure 12:
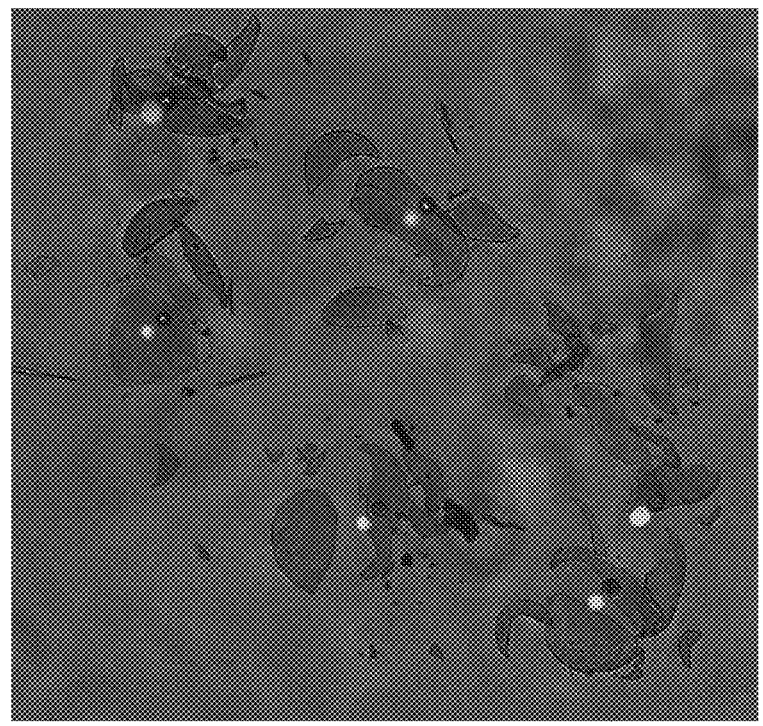
FIG. 12 image of cells obtained after punching out the bottom of the microwell and then further analyzed.

FIG. 12 shows an image of the microwell bottom containing 6 captured cells, labeled and punched out of the well and onto a slide for image analysis.

Point-of-Care Applications

Figure 13:
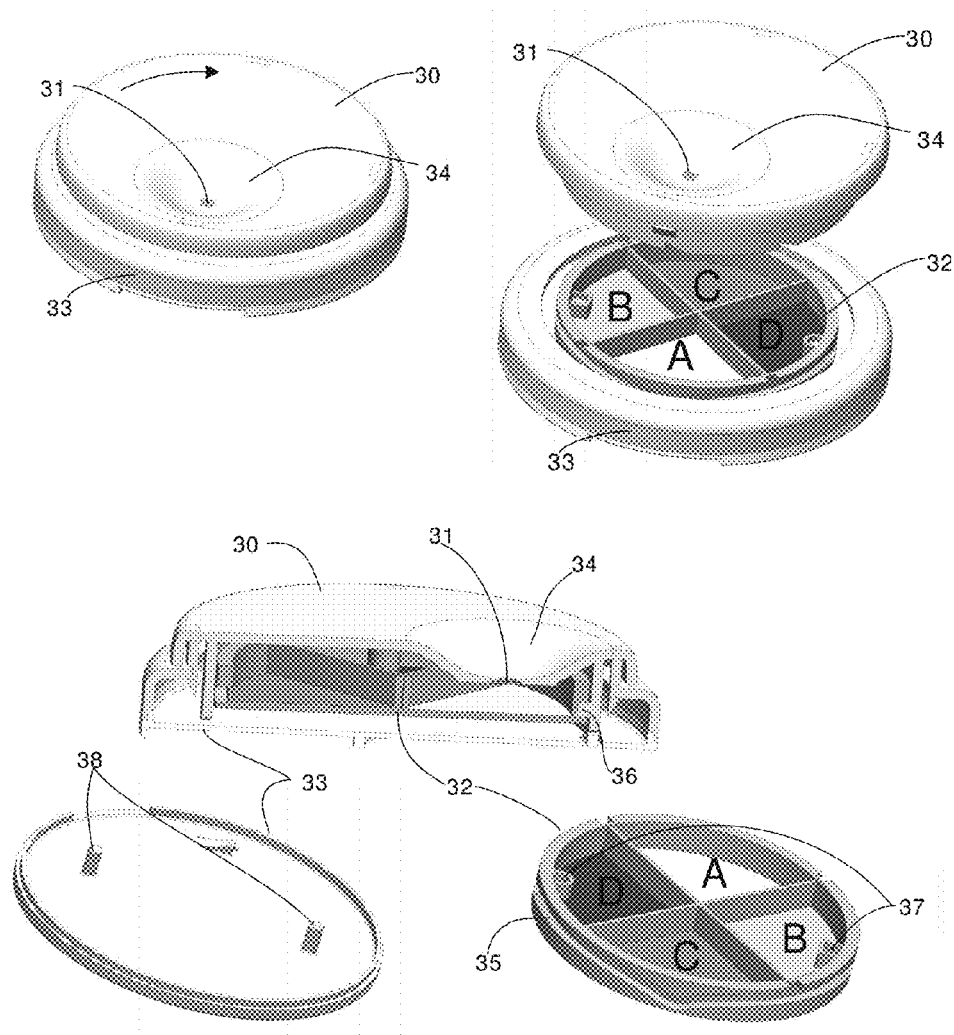
FIG. 13 shows one type of cartridge design containing four different compartments available for processing objects of interest.

The present invention is applicable as a diagnostic device in hospitals, clinics, or in any diagnostic setting where a medical test is conveniently and immediately provided for the patient, e.g. Point-of-Care. To be able to use the wettable microsieve in an efficient and easy to use manner as a point-of-care medical device, the microsieve needs to be mounted into a holder, a cartridge or a combination of both. While not intended to be limiting, one example for a cartridge design is shown in FIG. 13 and comprises a wettable microsieve, 31, comprising a monocrystalline silicon wafer, a silicon nitride layer, a silicon nitride membrane, and a porous absorbing material as diagramed in FIGS. 1 and 2. The microsieve is mounted at the bottom of a sample cup, 34, that can hold up to 20 ml of fluid. The cup is shaped as a funnel in the upper part of the cartridge, 30. The inside of the cartridge contains a disc, 32, sectioned into different compartments and able to move up and down inside the cartridge. The up and down motion of the disc is achieved by rotating the upper half of the cartridge in the direction indicated by the arrow. When rotating the disc, a set of pins, 36, connected to the upper half of the cartridge, 30, slides along the profile, 35, located on the side of the disc. The pins raise and lower the disc in the vertical direction along two bars, 38. These bars restrict the direction of motion to the vertical direction. This up and down movement results in making and breaking of the contact between the microsieve, and the contents of the compartment. The different compartments may contain absorbing bodies, reagents, reagent pouches and pads, wash buffers, etc. In the example shown in FIG. 13, the disc contains 4 compartments. The number of compartments is dependent upon the type of application and can be increased or decreased as required.

Sample analysis using a 4 compartment disc includes the following steps.

Step 1: Transferring a fluid sample containing cells, bacteria or other particles of interest into the sample cup, 34.

Step 2: By rotating the upper half of the cartridge, the microsieve and cup are moved towards the center of compartment A, shown in FIG. 13. Compartment A contains an absorbing body able to absorb all sample fluid volume. Rotating the upper half will force the pins, 36, to slide through the profile inducing a vertical movement of the disc towards the bottom of the microsieve, resulting in contact between the absorbing body and the bottom of the sieve. Sample fluid will flow towards the absorbing body as soon as contact between the bottom of the microsieve and the absorbing body is established.

Step 3: After all fluid passed through the sieve, cells or other objects of interest remain on the microsieve. By rotating the upper half of the cartridge, the microsieve moves to compartment B which contains reagents for cell analysis. While rotating the upper half of the cartridge, the disc is first lowered which breaks the continuity between the absorbing body and the microsieve. The disk will lift again with continued rotation as the microsieve approaches the center of compartment B, reaching its maximum when the microsieve is in the center of compartment B where it makes contact with the reagents. The reagents can be stored as discussed herein.

Step 4: The microsieve is brought into contact with the storage reagents. Reagents will flow towards the captured objects/cells as soon as contact between the storage reagent and bottom of the microsieve is established. The microsieve is left in contact with the storage reagent during incubation with the captured cells.

If storage of the reagents inside the cartridge is needed, compartment B can be left empty. For this situation, reagents need to be pipetted onto the microsieve. Because the compartment is empty and no contact exists between the microsieve and an absorption body, the reagents will not flow through the pores of the microsieve, allowing captured objects or cells to incubate with the added reagents as long as required.

Step 5: The microsieve is then moved to compartment C. Depending on the application this compartment can contain another absorbing body to remove access reagents from the microsieve or another set of reagents, wash buffers, or fixatives can be included for completing subsequent detailed analysis.

Step 6: Here the microsieve is moved towards compartment D. Depending on the type of application this compartment can contain another different set of reagents, wash buffers, fixatives, or absorbing bodies.

Figure 14:
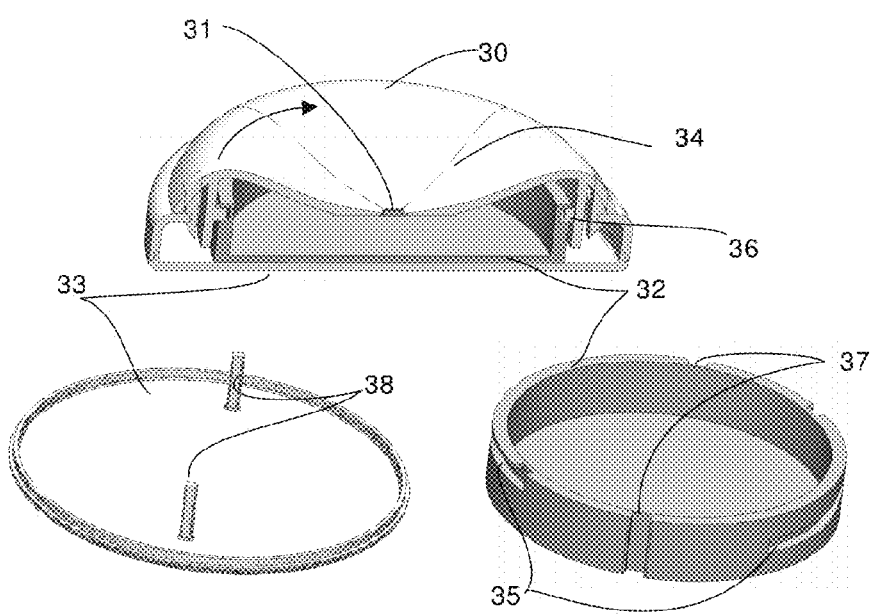
FIG. 14 shows a cartridge having a single compartment design.

Another embodiment of the cartridge provides a disc containing a single compartment useful in multipurpose analysis as shown in FIG. 14. This compartment will in general only contain an absorbing body. The wettable microsieve, 31, comprising a monocrystalline silicon wafer, a silicon nitride layer, a silicon nitride membrane, and a porous absorbing material, is present in the center of the cartridge at the bottom of the cup, 34, present in the upper part, 30, of the cartridge By rotating the upper part, 30, the pins, 36, slide along a groove, 35, thereby raising or lowering the disc in the vertical direction along the posts, 38, present on the bottom part of the cartridge, 33.

Raising the disc will induce contact between the absorbing body and the bottom of the microsieve, lowering the disc will break the contact.

Typically, a sample is transferred to the cup, 34. The upper part is next rotated in the direction indicated by the arrow in the image of FIG. 14. This will lift the disc inside the cartridge towards the bottom of the microsieve. The sample fluid starts flowing through the pores of the microsieve as soon as contact between the bottom of the microsieve and the absorbing body is established. After the fluid has passed the microsieve the continuity between microsieve and absorbing body is broken by rotating the upper part back to its start position. Reagents can now be added onto the microsieve for analysis of captured objects or cells. These reagents cannot flow through the sieve since no contact between microsieve and absorbing body exists. After the captured objects or cells have been incubated with the reagents and the reactions completed, the upper part is further rotated in the direction of the arrow, making contact again. Excess reagents will flow through the microsieve towards the absorbing body as soon as contact is established. This procedure can be repeated as many times as needed depending on the type of sample and type of analysis.

Figure 15:
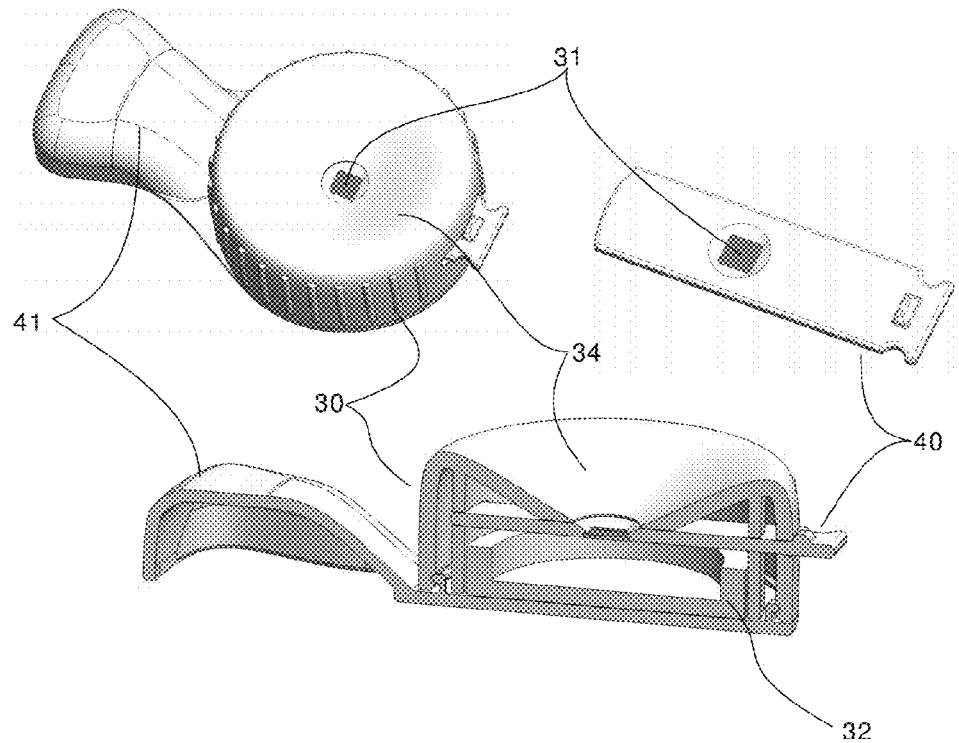
FIG. 15 shows a cartridge design with a removable slide containing a microsieve in a top view and in cross-section.

A further embodiment of the cartridge design incorporates the ability to remove the microsieve. While not limiting in the design, one example is the cartridge discussed above, but supplied with a removable slide, 40, containing the microsieve, 31 (FIG. 15). After the sample is transferred to the sample cup, 34, continuity between the absorbing body inside disc, 32, is established with the rotation of the upper half of the cartridge, 30, in the direction previously indicated. The sample fluid begins flowing through the wettable microsieve, 31, as soon as contact between absorbing body and bottom of the microsieve is established. Staining reagents can then be added. If incubation of the reagents with the objects of interest is required, the upper half is rotated back in order to break the contact again, allow for the reagents to be added. After staining, washing, fixation or other sample treatment steps have been performed, a slide containing the microsieve can be pulled out from the cartridge. A handle, 41, ensures easy manipulation of the cartridge while rotating the upper half and pulling out the slide. Next the slide can be transferred to a microscope, PCR cycler or other lab equipment or can be stored for later analysis.

Figure 16:
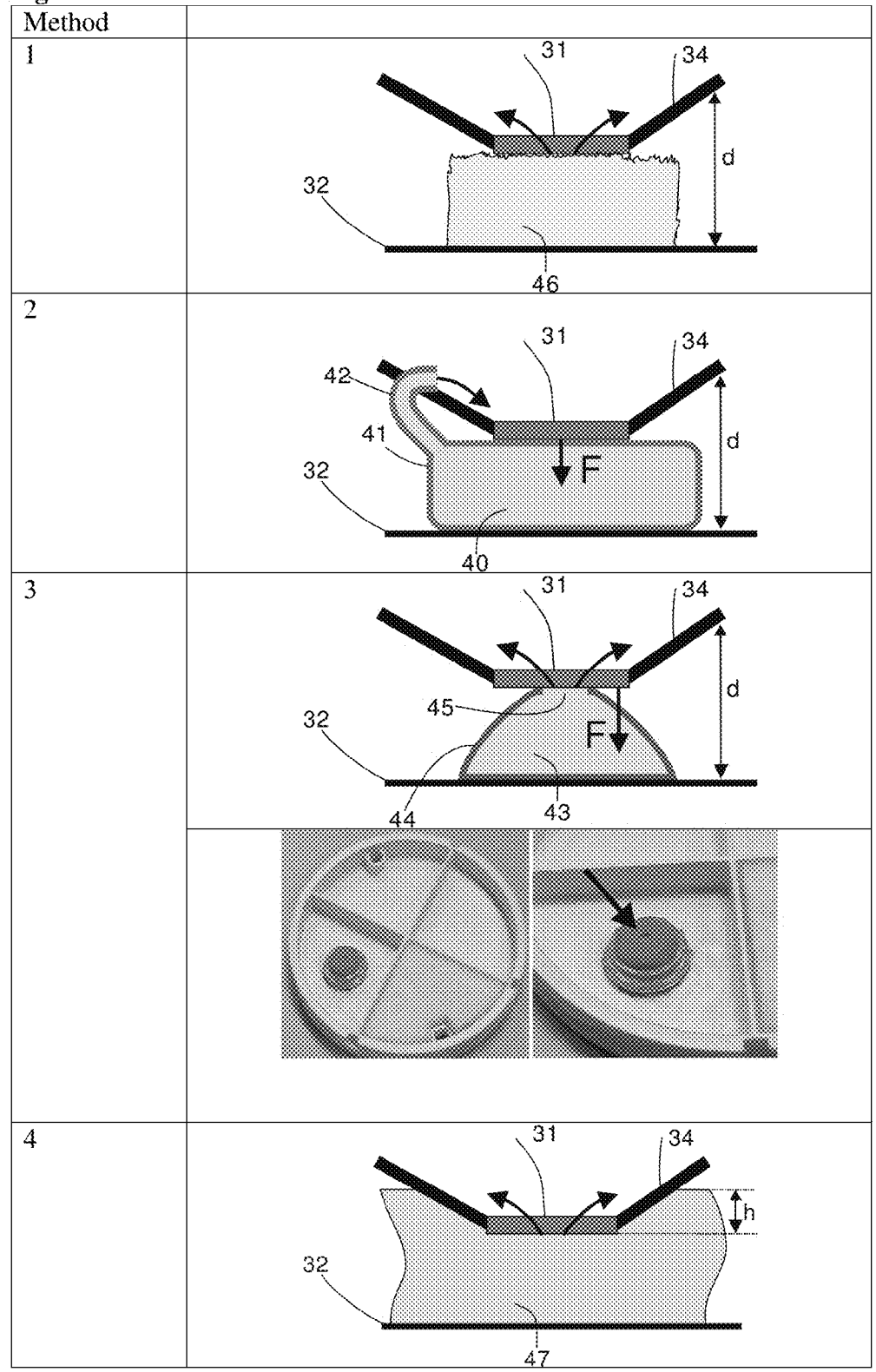
FIG. 16 diagrams for 5 separate types of methods used in reagents storage and transport inside the cartridge.

A further embodiment of the present invention includes reagent storage and transport methods for the microsieve. Reagents can be transported towards captured cells by one of methods depicted in FIG. 16.

Method 1: Reagent Pad

A pad, 46, saturated with reagents is placed in one of the compartments of the disc, 32, inside the cartridge. By decreasing the distance, d, between the disc bottom, 32, and the upper half of the cartridge, 34, the pad is pushed against the microsieve. The reagents will be transported by capillary forces and/or diffusion towards the cells collected on the microsieve.

Method 2: Pouch

A pouch, 41, filled with reagents, 40, is placed inside the cartridge onto the disc, 32. By decreasing the distance, d, between the disc bottom, 32, and the upper half of the cartridge, 34, a force (F) is applied onto the pouch. This will push the reagents through a connection, which can be a tube, 42, towards the collected cells. The pouch can be placed anywhere on the disc with no requirement to position the pouch directly under the microsieve.

Method 3: Enclosed Pouch

A sponge saturated with reagents, 43, is enclosed with a flexible watertight material such as rubber, 44. The enclosure has a small opening at the top, 45. This opening is smaller than the microsieve, 31. By decreasing the distance, d, between the disc bottom, 32, and the upper half of the cartridge, 34, the opening of the rubber enclosed sponge is pushed against the bottom of the microsieve creating a seal between the bottom of the microsieve and the rubber enclosure. By further decreasing distance d, pressure is build up inside the enclosed sponge. The reagents or fluids can only escape through the pores of the microsieve towards the collected objects or cells. The contact between the microsieve and the enclosure must be tight enough such that the fluid can only escape through the pores of the microsieve and not between the microsieve and rubber enclosure. The stiffness and rigidity of the microsieve will also facilitate the opening of sponge, 43, (or other sealed fluid reservoirs), when pushing forces are applied. Photographs in FIG. 16 (method 3) show a rubber enclosed pouch inside one of the disc compartments, 32. The arrow is pointing to the small opening in the enclosure. The microsieve area is connected to this small opening.

Method 4: Free Fluid

One of the compartments of the disc, 32, is filled with reagents in fluidic phase, 47. The microsieve, 31 is lowered into the reagents at a level such that the microsieve surface is below the surface of the fluid. The difference in height, h, within the cartridge, 34, creates a pressure across the microsieve sufficient to push the fluids through the microsieve surface.

Figure 17:
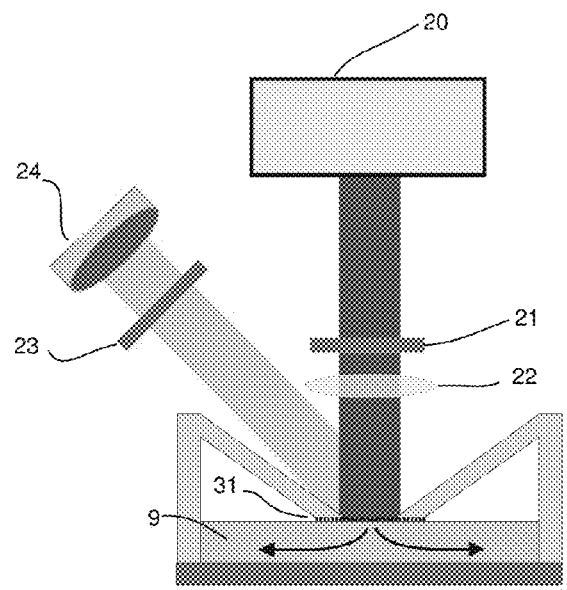
FIG. 17 is a schematic representation of an image cytometer in conjunction with the cartridge containing a microsieve as described in the present invention.

Applications of the present invention as a point-of-care medical device, capable of incorporating image cytometry, include, but not limited to, the analysis of cells having a low cell density and present in bodily fluids. Body fluids include, but not limited to, urine, spinal fluid, pleural and peritoneal fluid, bronchial aspirates and nasal swabs. The cells first need to be collected and prepared using the cartridge followed by analysis of captured or collected events. FIG. 17 is a schematic representation of an image cytometer, designed to be able to acquire a fluorescence image of the microsieve surface and characterize the cells present in the image based on their fluorescence color and/or intensity. The light of a fluorescence excitation light source, 24, is passing an excitation band pass filter, 23, and is focused onto the surface of the microsieve exciting the fluorescence labels of the collected events. When directly focusing the light onto the sample, the light can be guided by light guides or fibers towards the sample. The image in FIG. 19 was obtained with the excitation light focused directly onto the microsieve by a lens. Other optical configurations are possible for example an epi-fluorescence design or use fibers, light guides or other optical components to guide the light towards the microsieve surface.

The number of excitation wavelengths should match the number (fluorescence) of labels needed in the analysis. As shown in FIG. 17, the emitted fluorescence light is collected by an objective lens, 22, passed through an emission filter, 21, and projected on the surface of a CCD camera, 20. The CCD camera must have sufficient pixel density to identify individual objects of interest and a sensitivity that is able to differentiate the low fluorescence signal from the background.

Figure 18:
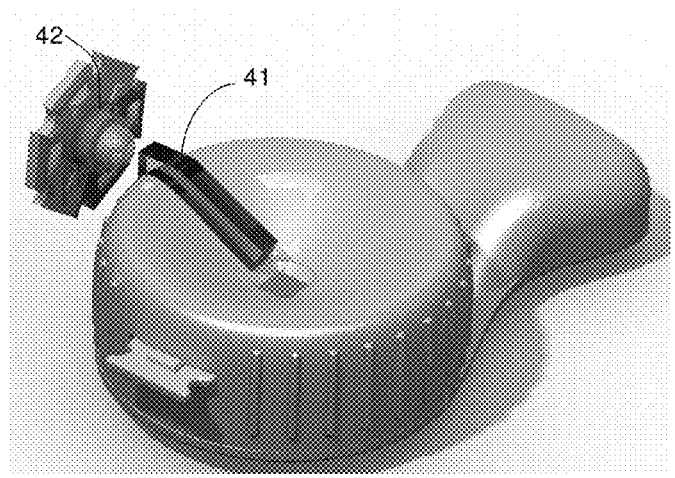
FIG. 18 shows the outside design of a cartridge with an integrated light guide to direct the excitation light towards the microsieve surface.

A further embodiment of the present invention integrates the cartridge with the optics. The image in FIG. 18 shows a cartridge with integrated light guide, 41, to direct light of the excitation source, in this case a light emitting diode (LED), 42, to the surface of the microsieve. This has the advantage that the angle of the excitation light path with the surface of the microsieve is small, thus reducing the amount of excitation light entering the emission path as well as creating the possibility of using "side scatter", a common parameter in cytometry, as an additional parameter to detect and differentiate the collected events.

The present invention has applications as a point-of-care analyzer in the evaluation of body fluid for the presence of disease.

Spinal Fluid

In general, spinal fluid is not stable, thus requiring rapid analysis. Current procedures require the collection of 1 to 5 ml of spinal fluid which is divided into aliquots and sent to the lab for analysis of cell content, glucose and/or protein.

In normal spinal fluid typically less than 5 leukocytes are detected per ml of spinal fluid. In disease conditions the number increases for example in cancer has 10-200 leukocytes or tumor cells/ml, autoimmune disease has 10-200 leukocytes per ml), viral meningitis has 100-1000 leukocytes (lymphocytes) per ml, and bacterial meningitis has greater than 1000 leukocytes (granulocytes) per ml.

The present invention is suitable for use at the patient's bed side for analysis of 1 ml of spinal fluid using a cartridge as described herein. The nucleic acid Acridine Orange is transferred from the reagent reservoir to the collected cells on the microsieve using one of the methods described herein. Excess reagent is removed by transferring the microsieve onto another absorbing body. Next the cartridge is placed on an image cytometer and an image of the microsieve is acquired and analyzed for the presence of nucleated cells. In alternative configurations the cells on the microsieve can be stained with multiple labels including fluorescently labeled monoclonal antibodies. For example in B cell malignancies, the cells on the microsieve are stained with a combination of anti-lambda Allophycocyan and anti-kappa PerCP. Excitation by red LED provides an image of cells stained with anti-lambda Allophycocyan and excitation by a blue LED provides an image of cells stained with anti-kappa PerCP. The presence of leukemic cells in the spinal fluid is established by the presence of either lambda positive or kappa positive cells on the microsieve.

Figure 19:
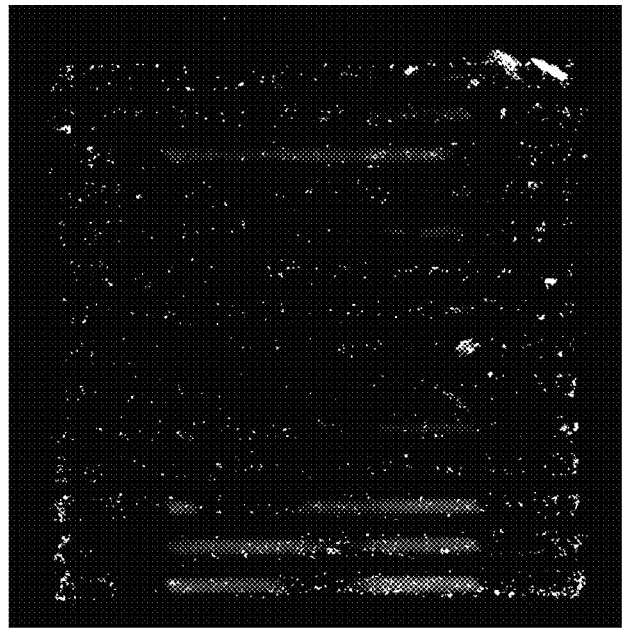
FIG. 19 shows a fluorescent image of cells captured on a microsieve. Cells are labeled with Acridine Orange.

The photograph in FIG. 19 shows a fluorescence image of cells present in 0.5 ml of spinal fluid collected onto a microsieve containing pores with a diameter of 2 μm. The microsieve is mounted in a cartridge with a disc containing 4 compartments. Compartment A contains an absorbing body, Compartment B contains an enclosed sponge containing Acridine Orange. Compartment C contains an absorbing body and compartment D was left empty. A sample volume of 0.5 milliliter spinal fluid is added to the sample cup onto the cartridge. The microsieve is turned towards compartment A, which starts the fluid transport towards the absorption body. After all fluid passes, the microsieve is turned towards compartment B which forces the reagents to move from the enclosed pouch through the bottom of the microsieve towards the cells. After incubation for 1 minute the microsieve is turned towards compartment C which contains another absorbing body. Finally the microsieve is turned to compartment D which is empty and the cartridge was placed under a fluorescence microscope to acquire the fluorescence image as shown in FIG. 19.

Pleural & Peritoneal Fluid

Similar to spinal fluid relatively few cells are found in lung or peritoneal fluids under normal circumstances, but in certain disease conditions cells are present in larger amounts. In a differential diagnosis, the composition of the cells becomes important especially for determining the presence of cancer(ous) cells. Pleural fluid may contain leukocytes, mesothelial cells and carcinoma cells, requiring discrimination between each. To differentiate between these cells, fluorescently labeled antibodies directed against EpCAM (present on carcinoma cells but not on mesothelial cells), cytokeratins (present on both carcinoma cells and mesothelial cells) and CD45 (present on only leukocytes) are used. After passage of the pleural fluid and staining of the cells, they are readily analyzed in detail using other reagents or more sophisticated analysis platforms such as a high-end fluorescent microscope.

Figure 20:
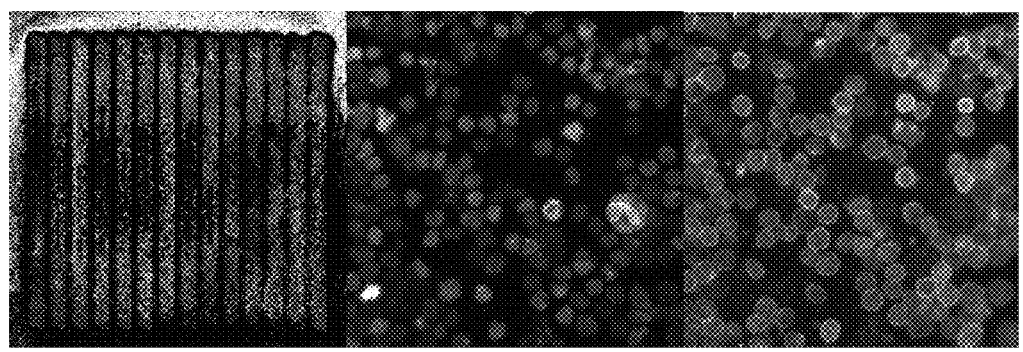
FIG. 20 are three panels of fluorescently imaged cells collected from pleural fluids. Panel A: image of Acridine Orange labeled cells acquired using a 4× magnification. Panel B: image of Acridine Orange fluorescence using a 40× magnification. Panel C: CD45-Allophycocyanin fluorescence using a 40× magnification.

FIG. 20 displays three fluorescence microscope images of cells isolated from pleura fluid using the cartridge design described herein containing a microsieve with pores having a diameter of 2 microns. After the filtration was completed, the contact between the microsieve and absorbing body was broken by rotating the upper half of the cartridge. Next the staining buffer, containing a mixture of Acridine Orange and CD45-Allophycocyanin, was added on the microsieve surface and the sample was incubated. After incubation, the contact between microsieve and absorbing body was reestablished, which removed the excess reagents. FIG. 20, panel A displays a 4× magnified fluorescence image the microsieve surface. The Acridine Orange fluorescence of the nuclei of the collected cells are visible as dots on the microsieve. FIG. 20, panel B shows a fluorescence image of the cells after staining the nuclei with Acridine Orange, using a 40× magnification. FIG. 20, panel C shows CD45-Allophycocyanin fluorescence of the area corresponding to FIG. 20, panel B.

Nasal Swabs

Nasal swabs are commonly used to detect the presence of organisms such as bacteria or virally infected cells such as Influenza A. The presence of a specific infectious agent is commonly detected after culturing the cells in the nasal swabs and staining the expanded cells with fluorescently labeled antibodies specific for the infectious agent. The device described in the present invention simplifies this procedure, by passing the nasal fluid through the microsieve. The epithelial cells and leukocytes are captured on the microsieve and are now easily stained with fluorescently labeled antibodies specific for the infectious agent. Typical infectious agents can include Influenza A, Influenza B, or respiratory virus.

Urine

FIG. 21 shows two fluorescence microscope images of cells isolated from a freshly obtained urine sample. The cartridge design described herein using a microsieve with pores of 2 microns was used. The urine sample was transferred to the sample cup and filtered. After the filtration was completed the contact between the microsieve and absorbing body was broken by rotating the upper half of the cartridge. Staining buffer containing Acridine Orange was deposited on the microsieve. After incubation, the contact between microsieve and absorbing body was reestablished to remove the excess reagents. FIG. 21, panel A show a 4× magnified fluorescence image of the whole surface of the microsieve. The image in FIG. 21, panel B further magnifies part of the image of FIG. 21, panel A. The cell nuclei are show as white dots. Though the intensity is weak the outer cell membranes are visible.

Research and Drug Discovery Applications

The present invention has applications in basic scientific research, providing cost-effective, rapid, and detailed cellular analysis. As seen from the image in FIG. 22, the cartridge as described herein can be used to assess SKBR-3 cells after they are collected and stained on a microsieve having pores with a diameter of 5 microns.

The microsieve is mounted in the cartridge as described previously. Compartment A contains an absorbing body, Compartment B contains an enclosed sponge filled with Acridine Orange, Compartment C contains an absorbing body, and compartment D is empty.

Two milliliters of cell suspension containing approximately 500 cells are added to a sample cup onto the cartridge. The microsieve is turned towards compartment A which starts the fluid transport towards the absorption body. After all fluid has passed, the microsieve is turned towards compartment B which forces the reagents to move from the enclosed pouch through the bottom of the microsieve towards the cells. After incubation for 1 minute the microsieve is turned towards compartment C which contained an absorption body. Next it was turned to compartment D which is empty and the cartridge is placed under the fluorescence microscope to acquire the fluorescence image shown in FIG. 22.

Another application of the present invention incorporates PCR or nucleic acid amplification reactions directly on the microsieve after cell capture. One embodiment for accomplishing this application requires reversing the orientation of the microsieve so the cavities are facing towards the sample fluid. The cavities will in this situation form wells that are used as a bio reagent chamber. A typical design is shown in FIG. 3, panel B where a silicon microsieve with round cavities having diameters of 100 microns, in a 3×3 mm$^2$ area have a bottom structure formed from the membrane of the microsieve which contains the pores. Further magnification of the pores is shown in FIG. 3, panel C. The membrane thickness usually is smaller than the diameter of the pores to achieve a low flow resistance. Here each cavity has only a single pore. When a cell enters the cavity it will occlude the pore, hereby enhancing the flow resistance and forcing other cells to enter a different cavity which decreases the chances that multiple cells are found in a single cavity.

A microsieve comprising such cavities is used for DNA analysis of individual cells present in very low densities. Examples include tumor cells present in body fluids, such as pleural, spinal and urine fluid. Amongst the tumor cells other, non-malignant cells are present in these fluids. To be able to analyze the DNA of the individual tumor cells it is important that their DNA is not mixed with DNA of other cells. As such the cell content from each of the collected cells is kept isolated for DNA analysis. Further, the top of cavity walls may be coated with an additional hydrophobic layer as an extra measure to prevent mixing of the contents of individual wells.

The present invention is applicable in PCR and Whole Genome Amplification followed by sequencing. These technologies are useful in detecting the presence of specific mutations which is relevant in identifying the disease type and can identify the therapy that is best suited for treatment. As discussed previously and shown in FIG. 10, methods are presented for collecting cells in the cavities of the microsieves, adding reagents and amplifying the DNA content in each of the cavities without contaminating neighboring cavities, followed by transferring the DNA to other instrumentation or analyze it directly on the microsieve.

The present invention is applicable in filtration, culturing and identification of microorganisms. A further embodiment of the present invention reduces the pore size of the microsieves, using the cavities to collect microorganisms. As previously described for DNA or RNA amplification, microorganisms captured in the cavities may be analyzed for DNA or RNA content. In addition, the reagents added for DNA amplification can be changed to a culturing medium which allows the collected bacteria to grow, followed by the identification of the collected bacteria.

The number of events or cells present in a sample is generally unknown. In some situations, the sample volume will contain more cells than the total number of pores present in the microsieve. Because these cells have diameters that are larger than the pore size, all the pores will become blocked before all fluid has passed through the microsieve. Thus the flow rate is reduced to practically zero resulting in sample fluid left behind on top of the microsieve, unable to pass through the microsieve. Consequently, the excess fluid must be removed before continuing with the staining of cells or subsequent steps, a situation that is highly unwanted.

To avoid this situation a microsieve is designed that contains pores with diameters that are smaller than the diameter of objects of interest but also contains pores with diameters larger than diameter of the largest object in the sample. Optimally the number of small pores is much larger than the number of large pores.

Figure 23:
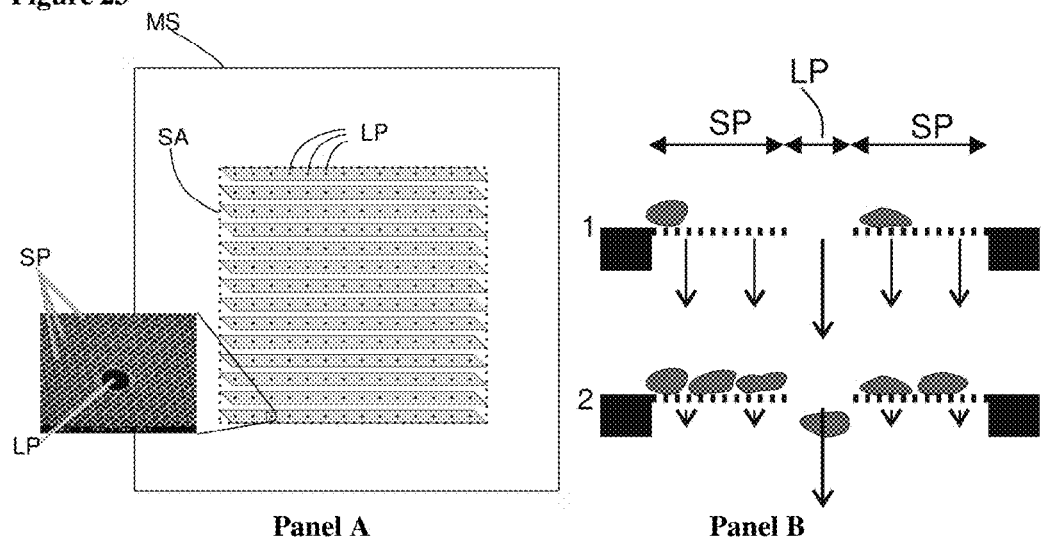
FIG. 23 depicts one type of design for spillway pores in the microsieve. Panel A shows the spillway pores are present across the entire sieve area (3×3 mm$^2$) and having a much lower density than the filtration pores. Panel B diagrams the filtration process incorporating the spillway pores. With a low flow resistance for the silicon microsieves, the presence of the larger holes does not affect the flow profile or cell capturing even when the number of cells or objects of interest is low. When the filtration pores become occupied the remaining sample fluid passes through the larger pores thus avoiding any clogging within the microsieve.

FIG. 23, panel A depicts a microsieve design with 800.000 normal filtration pores, SP, having a diameter of 2 microns which is smaller than the diameter of blood cells or other cell types having a slightly larger diameter. In addition 378 pores, LP, with a large diameter of 15 microns are present which enables the passage of objects that are larger than the diameter of targeted blood cells. In this example the silicon microsieve has a sieve area, SA, of 3×3 mm$^2$ and is divided in 14 membrane fields. Each membrane field contains 27 larger pores, LP, with a diameter of 15 microns that are located along the center line of membrane field and equally spaced at 107 microns. The insert shows a photograph of the microsieve membrane surface with small filtration pores, SP, and one large pore, LP, in the center of a membrane field.

Assuming that the flow rates through the small pores and large pores are independent of each other, the total flow rate that passes the microsieve membrane is the sum of the flow rates through the small pores plus the flow rate through the larger pores. When the microsieve is mounted into the cartridge described herein and brought into contact with the absorbent body, the flow rate through the large pores of the microsieve equals 0.2 ml/min. The maximum flow rate through the small pores, immediately after the sample was transferred into the sample cup onto the microsieve is equal to 1 ml/min. The flow through the small pores, SP, will however decrease when more cells are collected onto the microsieve membrane. This is schematically illustrated in FIG. 23, panel B. At the start of collection only a few cells have been captured on the microsieve and although the flow resistance of the area with the small pores, SP, is larger than that of the large pore, LP, the difference is relative small. The flow rate through the larger holes, LP, is larger but since the difference compared to the flow rate through the small pores is small, it has only very limited effect on the flow profile across the whole sieve. FIG. 23, panel B shows the flow rate schematically illustrated by the arrows with the length of each arrow indicating the flow rate. As more of the small pores become occupied with cells the flow rate though the small pores decreases. As soon as all the filtration pores are occupied by the cells the flow rate through the small pores, SP, becomes very small whereas the flow through the large pores, LP, remains constant since these remain unblocked. After all small pores, SP, are blocked the remainder of the sample will flow through the larger pores preventing excess sample fluid from being left on top of the microsieve. Together with the excess fluid, excess cells present in the excess sample fluid will pass through the large pores, LP.

Figure 24:
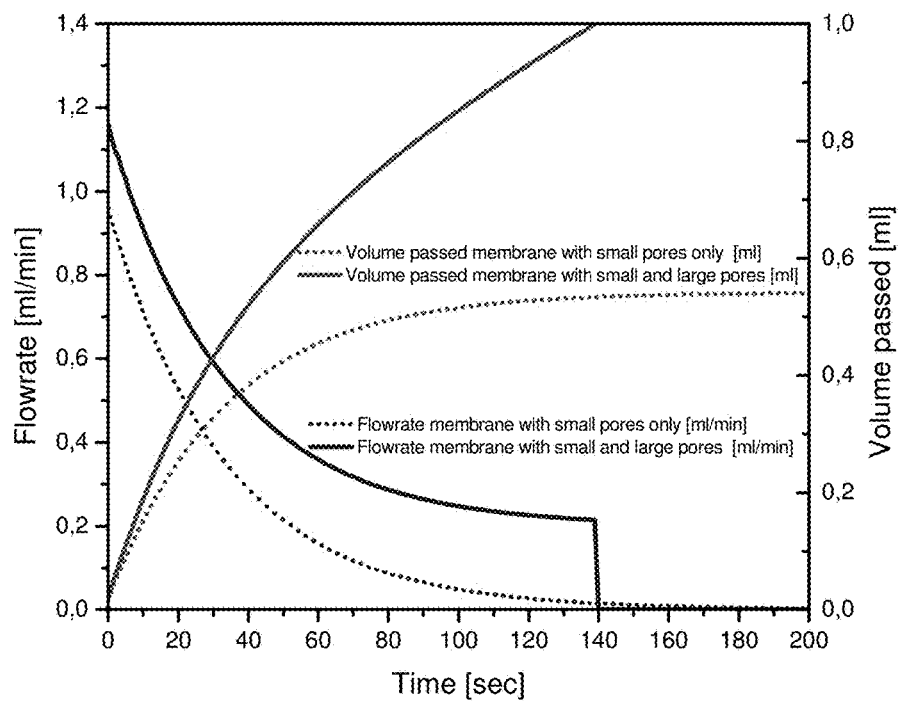
FIG. 24 shows a graph of the flow rate and volume passed for a standard microsieve and a microsieve with additional large pores. The number of events was set at 300000 and the sample volume at 1 ml. Dotted lines represent a microsieve having only 800.000 small pores each with a diameter of 2 microns. The solid lines represent a microsieve having an addition 378 large pores with a diameter of 15 microns.

The graph in FIG. 24 shows theoretical flow rates and the volume as a function of time as the sample passes through the microsieve. Microsieves containing only 800.000 small pores, SP, with a diameter of 2 microns are shown with dotted lines, while microsieves containing 378 additional large pores, LP, with a diameter of 15 microns are shown with a solid line. The graph represents the results using a sample volume of 1 ml and containing 300.000 cells having a diameter of 7 microns. The microsieve having small pores only resulted in a flow rate that decreases as more cells come in contact with the membrane, decreasing to virtually zero after 160 seconds (dotted blue line). The total volume able to pass through the microsieve in 200 seconds (dotted red line) equals 0.55 ml. The remainder of the sample, 0.45 ml, must to be removed from the sieve before proceeding with staining.

The solid blue and solid red lines represent the situation where the microsieve are supplied with an additional 378 large pores. Although the flow rate decreases over time the entire sample is able the pass through the microsieve in 140 seconds. Initially the flow rate through the small and large pores is approximately equal. As more small pores become occupied the flow rate through the small pores decrease whereas the flow rate through the large pores remains constant. With the passage of time, the volume that passes through the larger pores becomes larger with respect to the volume that passes through the small pores. After all the sample has passed through the microsieve, the proportion of sample volume passing through the small pores compared to the large pores is 0.45:0.55. Of the 300.000 cells applied to the microsieve, 135.000 cells have been captured onto the membrane.

Table 1 below shows the number of large pores needed to achieve a flow rate of 0.2 ml/min for different large pore diameters'

TABLE 1 number of large pores needed, as a function of its diameter, to achieve a flow rate of 0.2 ml/min through the large pores in the presence of 800.000 small pores with a diameter of 2 microns.

| Large pore diameter [um] | Number of pores | Percentage total area of the large pores/total area of the small pores |
|---|---|---|
| 15 | 379 | 0.67% |
| 20 | 160 | 0.50% |
| 25 | 81 | 0.40% |
| 30 | 47 | 0.33% |
| 40 | 20 | 0.25% |
| 50 | 10 | 0.20% |
| 100 | 1 | 0.10% |

To achieve a homogenous distribution of the large pores it is preferred to have large number of pores. This is best achieved by choosing the large pore diameter as small a possible but larger than the objects present in the sample capable of occluding the membrane.

A further embodiment of the present invention considers capturing objects of interest in a sample fluid with different dimensions. In this situation, a microsieve having pores with multiple dimensions may be used to collect these events.

Figure 25:
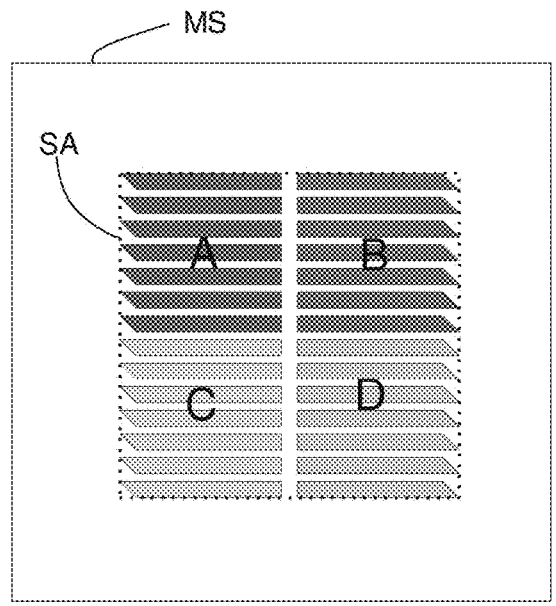
FIG. 25 represents one type of a design for a microsieve having a 5×5 mm$^2$ area with a the sieve area of 3×3 mm$^2$ containing four different fields A, B, C, D. Each field different pore diameters; field A at 0.45 microns, B at 2 microns, C at 4 microns, D at 6 microns.

FIG. 25 shows a microsieve design, MS, with an area of 5×5 mm$^2$, having a sieve area, SA, of 3×3 mm$^2$ that contains four different fields, A, B, C and D. Each field contains pores with a different diameter. Field A contains pores with a diameter of 0.45 microns which can be used for the detection of e.g. microorganisms and platelets, field B contains pores with a diameter of 2 micron, field C contains pores with a diameter of 4 microns and field D contains pores with a diameter of 6 microns. Depending on the sample type, the dimensions (including diameter and shape), the number of pores within each field, the number of different fields as well as the arrangement of the fields must be optimized to achieve the optimum result for different sample types. Instead of arranging the different pores in a specific area of the microsieve the different pore sizes may also be mixed and placed on any location along the microsieve. Further, each of the microsieve areas may be combined with the large pores.

The microsieve shown in FIG. 25 is applicable for collecting microorganisms, erythrocytes, white blood cells, tumor cells are collected in a single filtration step. The largest objects will be collected on all fields whereas the small objects will only be collected on the fields with the small pore dimensions. As such the (number) density of objects with the different diameters preferably will be as follows:
Density objects between 0.45-2 um≥Density objects between 2-4 um≥Density objects 4-6 um≥Density objects≥6 um.

Figure 26:
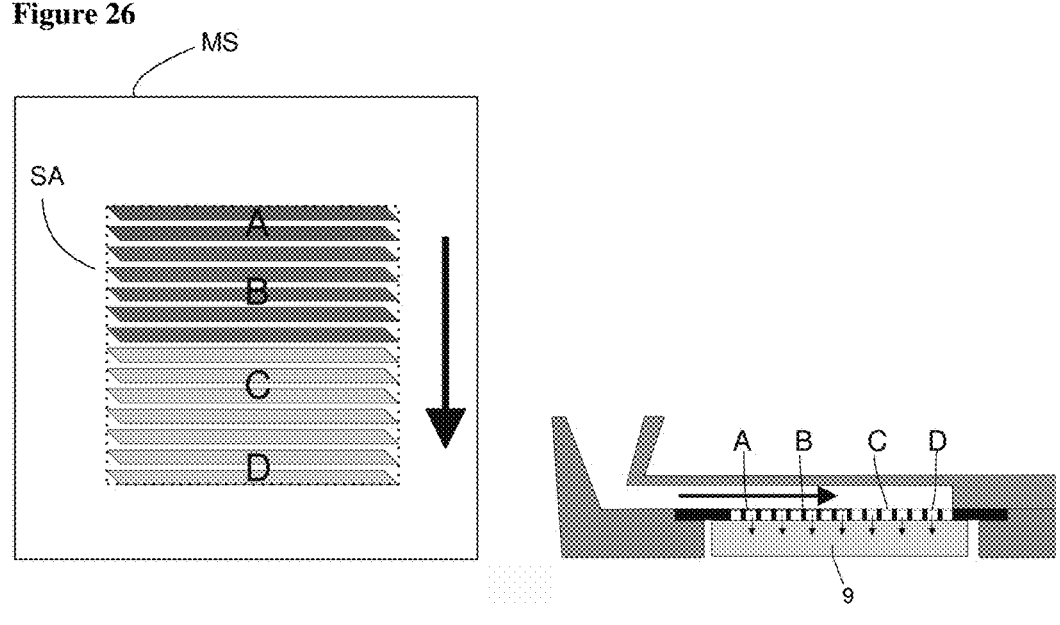
FIG. 26 represents another type of field orientation. Panel A represents the microsieve area divided into parallel 4 fields (A, B, C, D) each with different pore sizes perpendicular to the direction of flow. Pore diameter corresponds to the following: Field A=0.45 microns, Field B=2 microns, Field C=4 microns, Field D=6 microns. Panel B shows a side view of the flow in Panel A as mounted into a cartridge. The field with the smallest dimension, Field A, is positioned closest to the entrance of the sample fluid FIG. 27 Shows a schematic representation of a microfluidic chip in combination with a wettable microsieve in a Point of Care application using whole blood. Panel A depicts the cell suspension labeled with magnetic particles flowing through a fluidics channel, passing over the microsieve positioned above a magnet. Panel B shows an enlarged view of the microsieve and magnet area. After the sample passes the microsieve portion of the channel, an image of the microsieve area is acquired, Panel C.

A still further embodiment of the present invention incorporates the use as a cell sorter. FIG. 25 shows a microsieve with different pore dimensions positioned in each quadrant of the microsieve area. FIG. 26, panel A shows the microsieve area, SA, divided into four different fields A, B, C, and D with the fields placed in parallel to each other. FIG. 26, panel B shows a cross section of a flow channel inside a cartridge where the bottom of the flow channel is formed by the microsieve as depicted in FIG. 26, panel A. The cartridge contains an absorbing body that is comparable to the absorbing bodies used in the previous cartridge examples. The absorbing body induces the flow inside the channel. The sample is transferred into the flow channel and flows across the microsieve in the direction indicated by the arrow. Because of the self-wetting behavior of the microsieve the sample fluid passes through the pores. To create a horizontal flow towards field D, the flow resistance through the pores needs to be highest for field A and decreases towards field D. Field A contains the pores with the smallest diameter, in this example 0.45 microns, and the small objects are collected into the pores of this field. The horizontal shear force pushes the larger objects to the next fields. The objects most appropriate for the pores of field B have a diameter of 2 microns. Accordingly, they will stick there with the larger ones pushed towards field C under the influence of the shear force. The largest objects will be pushed to the end of the microsieve area which contains the largest pores with a diameter of 6 microns, field D.

Immunomagnetic Selection from Whole Blood in a Point-of-Care Diagnostic Device

A major problem with immunomagnetic enrichment of target cell types from body fluid is the presence of free unbound immune-magnetic particles, beads or ferrofluids. This limits the ability to inspect or interrogate the magnetically collected cells. In whole blood it becomes even more difficult since the unwanted blood components are also present and need to be removed by washing, lysing, etc.

In this example a wettable microsieve with a (micro) fluidic channel and a permanent magnet are combined to:
Magnetically collect immunomagnetically labeled cells onto the surface of the wettable microsieve by means of a permanent magnet.
Remove the excess unbound immunomagnetic ferrofluids.
Remove the excess blood components and make the cells visible for inspection.

FIG. 27, panel A illustrates a cross section of a fluidic chip comprising of a fluidic channel, a wettable microsieve, 31, a permanent magnet, 15, placed underneath the microsieve, 14. The sample is incubated with ferrofluids coupled to antibodies that recognize the cells or microorganism of interest. After the sample has been incubated it is transferred to the cartridge. The sample will flow through the channel and across the wettable microsieve. The area near the wettable microsieve and permanent magnet is depicted in FIG. 27, panel B. The immunomagnetically labeled cells, 18, will be captured onto the surface of the microsieve by magnetic force, while the non-labeled cells, 19, will flow across the sieve towards the absorbing material. The unbound excess immunomagnetic particles, 17, will be attracted by the magnet but since these are smaller they will pass through the microsieve surface towards the magnet. These immunomagnetic particles can only pass through the sieve membrane, 5, when fluid is present underneath the membrane making the wettable microsieve an essential component of this chip. The capillary forces of the absorbing material will absorb all the fluid from the fluidics channel clearing the channel from all blood components and allowing the captured events to be analyzed by microscopy, FIG. 27, panel C. When a "normal" not wettable microsieve is used the unbound ferrofluids will not move through the sieve membrane because no fluid is present underneath the microsieve and therefore cannot pass through the microsieve. The captured cells will in this case be covered under a layer of free unbound magnetic particles, limiting visible inspection to a large extent.

The system, apparatus and methods illustrated herein may suitably be practiced in the absence of any element or elements, limitation or limitation, not specifically disclosed herein. The terms and expressions used herein have been used as terms of description and not of limitation, and there is no intention in the use of such terms of excluding any equivalents of the features shown and described or portions thereof. It is recognized that various modification are possible within the scope of the invention claimed. Thus, it should be understood that although the present invention has been specifically disclosed by preferred embodiments and other features, modification and variation of the invention embodied therein herein disclosed may be used by those skilled in the art, and that such modification and variations are considered to be within the scope of this invention.

The invention claimed is:

1. A microwell plate for capturing an object of interest in a fluid sample comprising:
   a. a microwell plate having individual microwelis each with a bottom plate wherein at least one bottom plate has a single precisely etched pore to pass sample liquid from a supply side to a discharge side; and
   b. a means to apply a fluid sample to the supply side wherein the fluid sample contains an object of interest with a slightly larger diameter than the pore such that when the sample fluid is applied to the microwell the object of interest will occlude the pore.

2. The microwell plate according to claim 1, wherein the object of interest is a cell type capable of occluding the pore.

3. The microwell plate according to claim 1, wherein the bottom plate has a thickness around the pore less than ten times the diameter of the pore.

4. The microwell plate according to claim 3, wherein the bottom plate has a thickness around the pore less than three times the diameter of the pore.

5. The microwell plate according to claim 1, wherein the pore in the bottom plate are centered in the middle of the microwell.

6. The microwell plate according to claim 1, wherein the bottom plate comprises a silicon substrate and a thin ceramic membrane layer with the precisely etched pore.

7. The microwell plate according to claim 6, wherein the ceramic membrane layer is silicon nitride.

8. The microwell plate according to claim 1, wherein the microwell plate is chemically inert to prevent fluorescence back light scattering.

9. The microwell plate according to claim 1, further having a means for retrieving captured objects of interest.

10. The microwell plate of claim 9 wherein the retrieving means is by a punch-out means of the bottom plate or a pipetting means.

11. The bottom plate of claim 9 having a thickness between approximately 200 nm and 2 micrometers.

12. The microwell plate of claim 9, further having an interrogation means for individual objects of interest.

13. The microwell plate of claim 12 wherein the interrogation means is selected from a group consisting of DNA amplification means, RNA amplification means, FISH means, Whole Genome Amplification means, and combinations thereof.

14. The microwell plate of claim 1, wherein the supply side contains a hydrophobic layer to prevent mixing between individual microwells.

15. The microwell plate of claim 1 having further a sealing means to prevent cross contamination between microwells with the addition of reagents.

16. The sealing means of claim 15 using plastic foil, a fixating material or deposition of a hydrophobic agent.

17. The microwell plate of claim 1, wherein the microwell plate is used as a micro titer plate.

* * * * *